United States Patent
Lashinski

(10) Patent No.: US 10,849,755 B2
(45) Date of Patent: *Dec. 1, 2020

(54) MITRAL VALVE INVERSION PROSTHESES

(71) Applicant: MILLIPEDE, INC., Santa Rosa, CA (US)

(72) Inventor: Randall Lashinski, Windsor, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 68 days.

This patent is subject to a terminal disclaimer.

(21) Appl. No.: 15/423,374

(22) Filed: Feb. 2, 2017

(65) Prior Publication Data

US 2017/0143489 A1   May 25, 2017
US 2019/0269512 A9   Sep. 5, 2019

Related U.S. Application Data

(63) Continuation-in-part of application No. 14/427,909, filed as application No. PCT/US2013/059751 on Sep. 13, 2013, now Pat. No. 9,610,156.
(Continued)

(51) Int. Cl.
*A61F 2/24* (2006.01)

(52) U.S. Cl.
CPC .......... *A61F 2/2466* (2013.01); *A61F 2/2409* (2013.01); *A61F 2/2442* (2013.01);
(Continued)

(58) Field of Classification Search
CPC .... A61F 2/2409; A61F 2/2487; A61F 2/2466; A61F 2/24; A61F 2/848; A61F 2250/001;
(Continued)

(56) References Cited

U.S. PATENT DOCUMENTS 3,143,742 A   8/1964   Cromie
4,042,979 A   8/1977   Angell
(Continued)

FOREIGN PATENT DOCUMENTS

EP   0 624 080   12/2001
EP   1 872 743   1/2008
(Continued)

OTHER PUBLICATIONS

B. Braun Medical Inc., "Pulmonary Embolism: IVC Filters." Retrieved from the Internet: http://www.bbraunusa.com/pe/pe05a.html, 2004, 2 pages.
(Continued)

*Primary Examiner* — Dinah Baria

(57) ABSTRACT

Systems, devices and methods for resizing a valve annulus are described. An implant is delivered proximate a mitral valve, the implant comprising a tubular body and a plurality of piercing helical anchors, the tubular body comprising an proximal diameter and a distal diameter. Tissue proximate the mitral valve is engaged by rotating the plurality of anchors with corresponding rotational drivers. The tubular body may be transitioned from a first structural configuration having the proximal diameter smaller than the distal diameter to a second structural configuration having the proximal diameter larger than the distal diameter.

19 Claims, 24 Drawing Sheets

Related U.S. Application Data

(60) Provisional application No. 62/291,347, filed on Feb. 4, 2016, provisional application No. 61/700,989, filed on Sep. 14, 2012.

(52) U.S. Cl.
CPC .... *A61F 2/2445* (2013.01); *A61F 2220/0016* (2013.01); *A61F 2250/0039* (2013.01)

(58) Field of Classification Search
CPC ...... A61F 2220/0016; A61F 2002/8483; A61F 2/2442
See application file for complete search history.

(56) References Cited

U.S. PATENT DOCUMENTS

| | | |
|---|---|---|
| 4,290,151 A | 9/1981 | Massana |
| 4,602,911 A | 7/1986 | Ahmadi et al. |
| 4,820,299 A | 4/1989 | Philippe et al. |
| 5,064,431 A | 11/1991 | Gilbertson et al. |
| 5,254,127 A | 10/1993 | Wholey et al. |
| 5,370,685 A | 12/1994 | Stevens |
| 5,674,279 A | 10/1997 | Wright et al. |
| 5,674,280 A | 10/1997 | Davidson et al. |
| 5,769,816 A | 6/1998 | Barbut et al. |
| 5,772,590 A | 6/1998 | Webster, Jr. |
| 5,810,882 A | 9/1998 | Bolduc |
| 5,824,066 A | 10/1998 | Gross |
| 5,968,053 A | 10/1999 | Revelas |
| 5,984,959 A | 11/1999 | Robertson et al. |
| 6,001,127 A | 12/1999 | Schoon et al. |
| 6,059,731 A | 5/2000 | Seward et al. |
| 6,074,418 A | 6/2000 | Buchanan et al. |
| 6,176,877 B1 | 1/2001 | Buchanan et al. |
| 6,210,432 B1 | 4/2001 | Solem et al. |
| 6,254,642 B1 | 7/2001 | Taylor |
| 6,355,030 B1 | 3/2002 | Aldrich et al. |
| 6,402,780 B2 | 6/2002 | Williamson et al. |
| 6,582,460 B1 | 6/2003 | Cryer |
| 6,629,534 B1 | 10/2003 | Deem et al. |
| 6,652,537 B2 | 11/2003 | Mercereau et al. |
| 6,676,692 B2 | 1/2004 | Rabkin et al. |
| 6,695,878 B2 | 2/2004 | McGuckin et al. |
| 6,702,826 B2 | 3/2004 | Liddicoat et al. |
| 6,726,716 B2 | 4/2004 | Marquez |
| 6,730,121 B2 | 5/2004 | Ortiz et al. |
| 6,743,239 B1 | 6/2004 | Kuehn et al. |
| 6,776,791 B1 | 8/2004 | Stallings et al. |
| 6,786,925 B1 | 9/2004 | Schoon et al. |
| 6,790,231 B2 | 9/2004 | Liddicoat et al. |
| 6,805,710 B2 | 10/2004 | Bolling et al. |
| 6,824,562 B2 | 11/2004 | Mathis et al. |
| 6,875,231 B2 | 4/2005 | Anduiza et al. |
| 6,913,608 B2 | 7/2005 | Liddicoat et al. |
| 6,942,641 B2 | 9/2005 | Seddon |
| 6,942,694 B2 | 9/2005 | Liddicoat et al. |
| 6,951,571 B1 | 10/2005 | Srivastava |
| 6,964,684 B2 | 11/2005 | Ortiz et al. |
| 6,974,476 B2 | 12/2005 | McGuckin et al. |
| 6,986,775 B2 | 1/2006 | Morales et al. |
| 7,063,722 B2 | 1/2006 | Marquez |
| 7,007,698 B2 | 3/2006 | Thornton |
| 7,041,120 B2 | 5/2006 | Li et al. |
| 7,081,131 B2 | 7/2006 | Thornton |
| 7,087,064 B1 | 8/2006 | Hyde |
| 7,112,219 B2 | 9/2006 | Vidlund et al. |
| 7,160,322 B2 | 1/2007 | Gabbay |
| 7,166,127 B2 | 1/2007 | Spence et al. |
| 7,192,442 B2 | 3/2007 | Solam et al. |
| 7,247,134 B2 | 7/2007 | Vidlund et al. |
| 7,297,150 B2 | 11/2007 | Cartledge et al. |
| 7,323,004 B2 | 1/2008 | Parihar |
| 7,329,278 B2 | 2/2008 | Seguin et al. |
| 7,329,280 B2 | 2/2008 | Bolling et al. |
| 7,335,213 B1 | 2/2008 | Hyde et al. |
| 7,357,815 B2 | 4/2008 | Shaoulian et al. |
| 7,361,190 B2 | 4/2008 | Shaoulian et al. |
| 7,381,218 B2 | 6/2008 | Schreck |
| 7,404,824 B1 | 7/2008 | Webler et al. |
| 7,455,690 B2 | 11/2008 | Cartledge et al. |
| 7,482,936 B2 | 1/2009 | Bolling |
| 7,485,142 B2 | 2/2009 | Milo |
| 7,507,252 B2 | 3/2009 | Lashinski et al. |
| 7,527,646 B2 | 5/2009 | Randert et al. |
| 7,534,204 B2 | 5/2009 | Starksen |
| 7,556,647 B2 | 7/2009 | Drews et al. |
| 7,611,534 B2 | 11/2009 | Kapadia et al. |
| 7,637,946 B2 | 12/2009 | Solem et al. |
| 7,655,040 B2 | 2/2010 | Douk et al. |
| 7,674,222 B2 | 3/2010 | Nikolic et al. |
| 7,691,144 B2 | 4/2010 | Chang et al. |
| 7,695,510 B2 | 4/2010 | Bloom et al. |
| 7,722,667 B1 | 5/2010 | Buchanan |
| 7,731,649 B2 | 6/2010 | Ferrazzi |
| 7,740,638 B2 | 6/2010 | Hyde |
| D627,245 S | 11/2010 | Corn |
| 7,850,709 B2 | 12/2010 | Cummins et al. |
| 7,860,555 B2 | 12/2010 | Saadat |
| 7,887,582 B2 | 2/2011 | Mathis et al. |
| 7,896,913 B2 | 3/2011 | Damm et al. |
| 7,914,576 B2 | 3/2011 | Navia et al. |
| 7,914,577 B2 | 3/2011 | Cox |
| 7,927,371 B2 | 4/2011 | Navia et al. |
| 7,935,145 B2 | 5/2011 | Alfieri et al. |
| 7,959,673 B2 | 6/2011 | Carpentier et al. |
| 7,972,378 B2 | 7/2011 | Tabor et al. |
| 7,988,725 B2 | 8/2011 | Gross et al. |
| 7,993,395 B2 | 8/2011 | Vanermen et al. |
| 8,012,202 B2 | 9/2011 | Alameddine |
| 8,016,877 B2 | 9/2011 | Seguin et al. |
| 8,052,751 B2 | 11/2011 | Aklog et al. |
| 8,128,641 B2 | 3/2012 | Wardle |
| 8,142,494 B2 | 3/2012 | Randert et al. |
| 8,142,496 B2 | 3/2012 | Berreklouw |
| 8,157,853 B2 | 4/2012 | Laske et al. |
| 8,163,013 B2 | 4/2012 | Machold et al. |
| 8,182,528 B2 | 5/2012 | Salahieh et al. |
| 8,187,207 B2 | 5/2012 | Machold et al. |
| 8,187,324 B2 | 5/2012 | Webler et al. |
| 8,211,171 B2 | 7/2012 | Kim et al. |
| 8,226,707 B2 | 7/2012 | White |
| 8,277,502 B2 | 10/2012 | Miller et al. |
| 8,287,555 B2 | 10/2012 | Starksen et al. |
| 8,287,591 B2 | 10/2012 | Keidar et al. |
| 8,333,777 B2 | 12/2012 | Schaller et al. |
| 8,349,002 B2 | 1/2013 | Haifa et al. |
| 8,357,195 B2 | 1/2013 | Kuehn |
| 8,366,766 B2 | 2/2013 | Berreklouw |
| 8,382,653 B2 | 2/2013 | Dubi et al. |
| 8,430,926 B2 | 4/2013 | Kirson |
| 8,449,604 B2 | 5/2013 | Moaddeb et al. |
| 8,454,683 B2 | 6/2013 | Rafiee et al. |
| 8,480,733 B2 | 7/2013 | Navia et al. |
| 8,512,403 B2 | 8/2013 | Navia et al. |
| 8,551,161 B2 | 10/2013 | Dolan |
| 8,551,162 B2 | 10/2013 | Fogarty et al. |
| 8,560,009 B2 | 10/2013 | Etemad |
| 8,579,964 B2 | 11/2013 | Lane et al. |
| 8,603,159 B2 | 12/2013 | Seguin et al. |
| 8,608,797 B2 | 12/2013 | Gross et al. |
| 8,668,713 B2 | 3/2014 | Horan et al. |
| 8,673,001 B2 | 3/2014 | Cartledge et al. |
| 8,685,080 B2 | 4/2014 | White |
| 8,690,858 B2 | 4/2014 | Machold et al. |
| 8,690,939 B2 | 4/2014 | Miller et al. |
| 8,715,342 B2 | 5/2014 | Zipory et al. |
| 8,721,681 B2 | 5/2014 | Leung et al. |
| 8,721,718 B2 | 5/2014 | Kassab |
| 8,758,372 B2 | 6/2014 | Cartledge et al. |
| 8,778,021 B2 | 7/2014 | Cartledge |
| 8,784,482 B2 | 7/2014 | Randert et al. |
| 8,808,371 B2 | 8/2014 | Cartledge |
| 8,858,622 B2 | 10/2014 | Machold et al. |

(56) References Cited

U.S. PATENT DOCUMENTS

| | | |
|---|---|---|
| 8,864,823 B2 | 10/2014 | Cartledge et al. |
| 8,882,830 B2 | 11/2014 | Cartledge et al. |
| 8,906,046 B2 | 12/2014 | Anderson |
| 8,926,696 B2 | 1/2015 | Cabiri et al. |
| 8,940,042 B2 | 1/2015 | Miller et al. |
| 8,945,210 B2 | 2/2015 | Cartledge et al. |
| 8,956,407 B2 | 2/2015 | Macoviak et al. |
| 8,979,923 B2 | 3/2015 | Spence et al. |
| 8,979,925 B2 | 3/2015 | Chang et al. |
| 8,992,604 B2 | 3/2015 | Gross et al. |
| 8,998,979 B2 | 4/2015 | Seguin |
| 9,005,272 B2 | 4/2015 | White |
| 9,011,520 B2 | 4/2015 | Miller et al. |
| 9,023,065 B2 | 5/2015 | Bolduc et al. |
| 9,040,092 B2 | 5/2015 | Edelman et al. |
| 9,044,221 B2 | 6/2015 | Zentgraf et al. |
| 9,084,677 B2 | 7/2015 | Cartledge et al. |
| 9,095,277 B2 | 8/2015 | House |
| 9,101,338 B2 | 8/2015 | Hindrichs et al. |
| 9,107,749 B2 | 8/2015 | Bobo et al. |
| 9,107,750 B2 | 8/2015 | Cartledge et al. |
| 9,119,718 B2 | 9/2015 | Keranen |
| 9,138,315 B2 | 9/2015 | Straubinger et al. |
| 9,180,005 B1 | 11/2015 | Lashinski et al. |
| 9,192,471 B2 | 11/2015 | Bolling |
| 9,192,472 B2 | 11/2015 | Gross et al. |
| 9,198,755 B2 | 12/2015 | Shaolain et al. |
| 9,204,956 B2 | 12/2015 | Chanduszko et al. |
| 9,204,964 B2 | 12/2015 | Dahlgren et al. |
| 9,265,608 B2 | 2/2016 | Miller et al. |
| 9,301,756 B2 | 4/2016 | Wardle |
| 9,301,860 B2 | 4/2016 | White |
| 9,314,336 B2 | 4/2016 | Furnish et al. |
| 9,326,859 B2 | 5/2016 | Cartledge et al. |
| 9,339,379 B2 | 5/2016 | Quadri et al. |
| 9,351,830 B2 | 5/2016 | Gross et al. |
| RE46,126 E | 8/2016 | Kirson |
| RE46,127 E | 8/2016 | Kirson |
| 9,421,099 B2 | 8/2016 | Dolan |
| 9,427,215 B2 | 8/2016 | Cartledge et al. |
| 9,439,763 B2 | 9/2016 | Geist et al. |
| 9,474,606 B2 | 10/2016 | Zipory et al. |
| 9,492,276 B2 | 11/2016 | Lee et al. |
| 9,504,572 B2 | 11/2016 | Mauch et al. |
| 9,566,178 B2 | 2/2017 | Cartledge et al. |
| 9,585,747 B2 | 3/2017 | Quadri et al. |
| 9,592,122 B2 | 3/2017 | Zipory et al. |
| 9,597,184 B2 | 3/2017 | Machold et al. |
| 9,610,156 B2 | 4/2017 | Lashinski |
| 9,616,197 B2 | 4/2017 | Serina |
| 9,713,530 B2 | 7/2017 | Cabiri et al. |
| 9,730,790 B2 | 8/2017 | Quadri et al. |
| 9,744,038 B2 | 8/2017 | Dahlgren et al. |
| 9,775,709 B2 | 10/2017 | Miller et al. |
| 9,788,941 B2 | 10/2017 | Hacohen |
| 9,801,714 B2 | 10/2017 | White |
| 9,827,093 B2 | 11/2017 | Cartledge et al. |
| 9,848,983 B2 | 12/2017 | Lashinski et al. |
| 9,861,475 B2 | 1/2018 | Machold et al. |
| 9,872,769 B2 | 1/2018 | Gross et al. |
| 9,883,943 B2 | 2/2018 | Gross et al. |
| 9,974,653 B2 | 5/2018 | Gross et al. |
| 2001/0044637 A1 | 11/2001 | Jacobs et al. |
| 2002/0002401 A1 | 1/2002 | McGuckin et al. |
| 2002/0042621 A1 | 4/2002 | Liddicoat et al. |
| 2002/0072710 A1* | 6/2002 | Stewart ............ A61M 25/0082 604/164.02 |
| 2002/0151961 A1 | 10/2002 | Lashinski et al. |
| 2002/0161377 A1 | 10/2002 | Rabkin |
| 2002/0173841 A1 | 11/2002 | Ortiz et al. |
| 2002/0183837 A1 | 12/2002 | Streeter et al. |
| 2003/0040793 A1 | 2/2003 | Marquez |
| 2003/0050693 A1 | 3/2003 | Quijano et al. |
| 2003/0083742 A1 | 5/2003 | Spence et al. |
| 2003/0093148 A1 | 5/2003 | Bolling |
| 2003/0158570 A1 | 8/2003 | Ferrazzi |
| 2003/0199974 A1 | 10/2003 | Lee et al. |
| 2003/0199975 A1 | 10/2003 | Gabbay |
| 2003/0199987 A1 | 10/2003 | Berg et al. |
| 2003/0212453 A1 | 11/2003 | Mathis et al. |
| 2003/0225420 A1 | 12/2003 | Wardle |
| 2003/0233142 A1 | 12/2003 | Morales et al. |
| 2004/0010275 A1 | 1/2004 | Jacobs et al. |
| 2004/0049266 A1 | 3/2004 | Anduiza et al. |
| 2004/0186566 A1 | 3/2004 | Hindrichs et al. |
| 2004/0067544 A1 | 4/2004 | Vogel et al. |
| 2004/0092965 A1 | 5/2004 | Parihar |
| 2004/0122516 A1 | 6/2004 | Fogarty et al. |
| 2004/0127982 A1 | 7/2004 | Machold et al. |
| 2004/0133274 A1 | 7/2004 | Webler et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0167620 A1 | 8/2004 | Ortiz et al. |
| 2004/0172063 A1 | 9/2004 | Li et al. |
| 2004/0186565 A1 | 9/2004 | Schreck |
| 2004/0193191 A1 | 9/2004 | Starksen et al. |
| 2004/0193261 A1 | 9/2004 | Berreklouw |
| 2004/0236419 A1 | 11/2004 | Milo |
| 2004/0243104 A1 | 12/2004 | Seddon |
| 2004/0243227 A1 | 12/2004 | Starksen et al. |
| 2004/0243230 A1 | 12/2004 | Navia et al. |
| 2004/0249400 A1 | 12/2004 | Vargas et al. |
| 2004/0249453 A1 | 12/2004 | Cartledge et al. |
| 2004/0260394 A1 | 12/2004 | Douk et al. |
| 2005/0004665 A1 | 1/2005 | Aklog |
| 2005/0004668 A1 | 1/2005 | Aklog et al. |
| 2005/0038508 A1 | 2/2005 | Gabbay |
| 2005/0049692 A1 | 3/2005 | Numamoto |
| 2005/0075713 A1 | 4/2005 | Biancucci et al. |
| 2005/0080454 A1 | 4/2005 | Drews et al. |
| 2005/0119734 A1 | 6/2005 | Spence et al. |
| 2005/0131533 A1 | 6/2005 | Alfieri et al. |
| 2005/0137701 A1 | 6/2005 | Salahieh et al. |
| 2005/0177180 A1 | 8/2005 | Kaganov et al. |
| 2005/0182290 A1 | 8/2005 | Lau et al. |
| 2005/0182486 A1 | 8/2005 | Gabbay |
| 2005/0192629 A1 | 9/2005 | Saadat et al. |
| 2005/0197696 A1 | 9/2005 | Gomez |
| 2005/0234508 A1 | 10/2005 | Cummins et al. |
| 2005/0250986 A1 | 11/2005 | Rothe et al. |
| 2005/0267560 A1 | 12/2005 | Bates |
| 2005/0267572 A1 | 12/2005 | Schoon et al. |
| 2005/0288776 A1 | 12/2005 | Shaoulian et al. |
| 2005/0288783 A1 | 12/2005 | Shaoulian et al. |
| 2006/0015178 A1 | 1/2006 | Moaddeb et al. |
| 2006/0020332 A1 | 1/2006 | Lashinsky et al. |
| 2006/0025854 A1 | 2/2006 | Lashinski et al. |
| 2006/0025855 A1 | 2/2006 | Lashinski et al. |
| 2006/0025858 A1 | 2/2006 | Alameddine |
| 2006/0069429 A1 | 3/2006 | Spence |
| 2006/0100699 A1 | 5/2006 | Vidlund et al. |
| 2006/0106305 A1 | 5/2006 | Lau |
| 2006/0106456 A9 | 5/2006 | Machold et al. |
| 2006/0129235 A1 | 6/2006 | Seguin et al. |
| 2006/0149349 A1 | 7/2006 | Garbe |
| 2006/0149368 A1 | 7/2006 | Spence |
| 2006/0178733 A1 | 8/2006 | Pinchuk et al. |
| 2006/0184240 A1 | 8/2006 | Jimenez et al. |
| 2006/0184241 A1 | 8/2006 | Marquez |
| 2006/0195012 A1 | 8/2006 | Mortier et al. |
| 2006/0206203 A1 | 9/2006 | Yang et al. |
| 2006/0229708 A1 | 10/2006 | Powell et al. |
| 2006/0241746 A1 | 10/2006 | Shaoulian et al. |
| 2006/0241747 A1 | 10/2006 | Shaoulian et al. |
| 2006/0241748 A1 | 10/2006 | Lee et al. |
| 2006/0282161 A1 | 12/2006 | Huynh et al. |
| 2006/0282162 A1 | 12/2006 | Nguyen et al. |
| 2007/0005129 A1 | 1/2007 | Damm et al. |
| 2007/0016287 A1 | 1/2007 | Cartledge et al. |
| 2007/0016288 A1 | 1/2007 | Gurskis et al. |
| 2007/0027533 A1 | 2/2007 | Douk |
| 2007/0027536 A1 | 2/2007 | Mihaljevic et al. |
| 2007/0049942 A1 | 3/2007 | Hindrichs et al. |

(56) References Cited

U.S. PATENT DOCUMENTS

| | | |
|---|---|---|
| 2007/0050019 A1 | 3/2007 | Hyde |
| 2007/0055368 A1 | 3/2007 | Rhee et al. |
| 2007/0083259 A1 | 4/2007 | Bloom et al. |
| 2007/0093890 A1 | 4/2007 | Eliasen et al. |
| 2007/0112423 A1 | 5/2007 | Chu |
| 2007/0112425 A1 | 5/2007 | Schaller et al. |
| 2007/0142907 A1 | 6/2007 | Moaddeb et al. |
| 2007/0156233 A1 | 7/2007 | Kapadia et al. |
| 2007/0161846 A1 | 7/2007 | Nikolic et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0265701 A1 | 11/2007 | Gurskis et al. |
| 2007/0276478 A1 | 11/2007 | Marmureanu et al. |
| 2007/0282436 A1 | 12/2007 | Pinchuk |
| 2007/0293942 A1 | 12/2007 | Mirzaee |
| 2007/0299543 A1 | 12/2007 | Cartledge et al. |
| 2008/0027483 A1 | 1/2008 | Cartledge et al. |
| 2008/0067713 A1 | 3/2008 | Bordener |
| 2008/0071364 A1 | 3/2008 | Kaye et al. |
| 2008/0077235 A1 | 3/2008 | Kirson |
| 2008/0177380 A1 | 7/2008 | Starksen et al. |
| 2008/0255661 A1 | 10/2008 | Straubinger et al. |
| 2008/0262609 A1 | 10/2008 | Gross |
| 2008/0288060 A1 | 11/2008 | Kaye et al. |
| 2009/0082857 A1 | 3/2009 | Lashinski et al. |
| 2009/0087414 A1 | 4/2009 | Edelman et al. |
| 2009/0149872 A1 | 6/2009 | Gross et al. |
| 2009/0177276 A1 | 7/2009 | Carpentier et al. |
| 2009/0182419 A1 | 7/2009 | Bolling |
| 2009/0198316 A1 | 8/2009 | Laske et al. |
| 2009/0264996 A1 | 10/2009 | Vanermen et al. |
| 2009/0276040 A1 | 11/2009 | Rowe et al. |
| 2009/0287299 A1 | 11/2009 | Tabor et al. |
| 2009/0287304 A1 | 11/2009 | Dahlgren et al. |
| 2009/0306622 A1 | 12/2009 | Machold |
| 2010/0004740 A1 | 1/2010 | Sequin et al. |
| 2010/0049315 A1 | 2/2010 | Kirson |
| 2010/0087855 A1 | 4/2010 | Leung et al. |
| 2010/0100174 A1 | 4/2010 | Gurskis |
| 2010/0121433 A1 | 5/2010 | Bolling |
| 2010/0152838 A1 | 6/2010 | Kang et al. |
| 2010/0152840 A1 | 6/2010 | Seguin et al. |
| 2010/0152845 A1 | 6/2010 | Bloom et al. |
| 2010/0185229 A1 | 7/2010 | Horan |
| 2010/0249920 A1 | 9/2010 | Bolling |
| 2010/0280604 A1 | 11/2010 | Zipory et al. |
| 2010/0298929 A1 | 11/2010 | Thornton |
| 2011/0022166 A1 | 1/2011 | Dahlgren et al. |
| 2011/0060407 A1 | 3/2011 | Ketai et al. |
| 2011/0066224 A1 | 3/2011 | White |
| 2011/0066236 A1 | 3/2011 | Khalapyan |
| 2011/0106245 A1 | 5/2011 | Miller et al. |
| 2011/0106247 A1 | 5/2011 | Miller et al. |
| 2011/0166649 A1 | 7/2011 | Gross et al. |
| 2011/0172760 A1 | 7/2011 | Anderson |
| 2011/0190879 A1 | 8/2011 | Bobo et al. |
| 2011/0202127 A1 | 8/2011 | Mauch et al. |
| 2011/0219603 A1 | 9/2011 | White |
| 2011/0224785 A1 | 9/2011 | Hacohen |
| 2011/0230956 A1 | 9/2011 | White |
| 2011/0230961 A1 | 9/2011 | Langer et al. |
| 2011/0288632 A1 | 11/2011 | White |
| 2011/0319989 A1 | 12/2011 | Lane et al. |
| 2012/0022640 A1 | 1/2012 | Gross et al. |
| 2012/0027116 A1 | 2/2012 | Etemad |
| 2012/0053680 A1 | 3/2012 | Bolling et al. |
| 2012/0109288 A1 | 5/2012 | Bolling |
| 2012/0109289 A1 | 5/2012 | Bolling |
| 2012/0197388 A1 | 8/2012 | Khairkhahan et al. |
| 2012/0203330 A1 | 8/2012 | Cartledge et al. |
| 2012/0209379 A1 | 8/2012 | Shaolian et al. |
| 2012/0215303 A1 | 8/2012 | Quadri |
| 2012/0283757 A1 | 11/2012 | Miller et al. |
| 2012/0308610 A1 | 12/2012 | Edelman et al. |
| 2013/0006295 A1 | 1/2013 | Chanduszko |
| 2013/0030523 A1 | 1/2013 | Padala et al. |
| 2013/0046373 A1 | 2/2013 | Cartledge |
| 2013/0123910 A1 | 5/2013 | Cartledge et al. |
| 2013/0123913 A1 | 5/2013 | Kuehn |
| 2013/0138207 A1 | 5/2013 | Quadri |
| 2013/0144380 A1 | 6/2013 | Quadri et al. |
| 2013/0177600 A1 | 7/2013 | Edelman et al. |
| 2013/0226289 A1 | 8/2013 | Shaolian et al. |
| 2013/0289710 A1* | 10/2013 | Leedle ............... A61B 17/0644 623/1.24 |
| 2013/0296999 A1 | 11/2013 | Burriesci et al. |
| 2013/0325118 A1 | 12/2013 | Cartledge |
| 2014/0018913 A1 | 1/2014 | Cartledge et al. |
| 2014/0039612 A1 | 2/2014 | Dolan |
| 2014/0142695 A1 | 5/2014 | Gross et al. |
| 2014/0163690 A1 | 6/2014 | White |
| 2014/0222136 A1 | 8/2014 | Geist et al. |
| 2014/0277427 A1 | 9/2014 | Ratz et al. |
| 2014/0277563 A1 | 9/2014 | White |
| 2014/0296962 A1 | 10/2014 | Cartledge et al. |
| 2014/0309731 A1 | 10/2014 | Quadri et al. |
| 2014/0336756 A1 | 11/2014 | Lee et al. |
| 2015/0081014 A1 | 3/2015 | Gross et al. |
| 2015/0112432 A1 | 4/2015 | Reich et al. |
| 2015/0127096 A1 | 5/2015 | Rowe et al. |
| 2015/0142105 A1 | 5/2015 | Bolling et al. |
| 2015/0148896 A1 | 5/2015 | Karapetian |
| 2015/0157459 A1 | 6/2015 | Macoviak |
| 2015/0250461 A1 | 9/2015 | Berreklouw |
| 2016/0008130 A1 | 1/2016 | Hasin |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0038285 A1 | 2/2016 | Glenn et al. |
| 2016/0095704 A1 | 4/2016 | Whitman |
| 2016/0120645 A1 | 5/2016 | Alon |
| 2016/0128829 A1 | 5/2016 | Oba |
| 2016/0235526 A1 | 8/2016 | Lashinski et al. |
| 2016/0256276 A1 | 9/2016 | Yaron |
| 2016/0317304 A1 | 11/2016 | Spence et al. |
| 2016/0324638 A1 | 11/2016 | Dolan et al. |
| 2016/0346084 A1 | 12/2016 | Taylor et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0035562 A1 | 2/2017 | Quadri |
| 2017/0035564 A1 | 2/2017 | Ryan |
| 2017/0049570 A1 | 2/2017 | O'Beirne et al. |
| 2017/0086974 A1 | 3/2017 | Lashinski et al. |
| 2017/0143488 A1 | 5/2017 | Lashinski et al. |
| 2017/0156860 A1 | 6/2017 | Lashinski et al. |
| 2017/0209253 A1 | 7/2017 | Lashinski et al. |
| 2017/0231759 A1 | 8/2017 | Geist |
| 2017/0348098 A1 | 12/2017 | Rowe et al. |
| 2017/0360549 A1 | 12/2017 | Lashinski et al. |
| 2017/0367825 A1 | 12/2017 | Cabiri et al. |
| 2018/0014934 A1 | 1/2018 | Miller et al. |
| 2018/0028311 A1 | 2/2018 | Hacohen et al. |
| 2018/0085217 A1 | 3/2018 | Lashinski et al. |
| 2018/0228610 A1 | 8/2018 | Lashinski et al. |
| 2018/0263776 A1 | 9/2018 | Gross et al. |
| 2018/0263777 A1 | 9/2018 | Gross et al. |

FOREIGN PATENT DOCUMENTS

| | | |
|---|---|---|
| EP | 2 047 824 | 5/2012 |
| EP | 2 656 816 | 10/2013 |
| JP | 2008-538937 | 11/2008 |
| JP | 2010-284536 | 12/2010 |
| WO | WO 90/09153 | 8/1990 |
| WO | WO 93/15690 | 8/1993 |
| WO | WO 97/12565 | 4/1997 |
| WO | WO 97/20524 | 6/1997 |
| WO | WO 98/24386 | 6/1998 |
| WO | WO 99/29269 | 6/1999 |

(56) References Cited

FOREIGN PATENT DOCUMENTS

| | | |
|---|---|---|
| WO | WO 99/49816 | 10/1999 |
| WO | WO 00/07521 | 2/2000 |
| WO | WO 00/18333 | 4/2000 |
| WO | WO 00/44311 | 8/2000 |
| WO | WO 00/62715 | 10/2000 |
| WO | WO 01/89440 | 11/2001 |
| WO | WO 02/034121 | 5/2002 |
| WO | WO 02/094132 | 11/2002 |
| WO | WO 03/017874 | 3/2003 |
| WO | WO 03/053289 | 7/2003 |
| WO | WO 03/080150 | 10/2003 |
| WO | WO 03/105670 | 12/2003 |
| WO | WO 03/105730 | 12/2003 |
| WO | WO 04/014282 | 2/2004 |
| WO | WO 04/019816 | 3/2004 |
| WO | WO 04/019826 | 3/2004 |
| WO | WO 04/030569 | 4/2004 |
| WO | WO 04/031717 | 4/2004 |
| WO | WO 04/032717 | 4/2004 |
| WO | WO 04/082538 | 9/2004 |
| WO | WO 04/103223 | 12/2004 |
| WO | WO 04/112657 | 12/2004 |
| WO | WO 05/002424 | 1/2005 |
| WO | WO 05/007037 | 1/2005 |
| WO | WO 05/046488 | 5/2005 |
| WO | WO 05/087139 | 9/2005 |
| WO | WO 06/011275 | 2/2006 |
| WO | WO 06/052687 | 5/2006 |
| WO | WO 06/086135 | 8/2006 |
| WO | WO 06/086434 | 8/2006 |
| WO | WO 06/105084 | 10/2006 |
| WO | WO 06/116129 | 11/2006 |
| WO | WO 06/116357 | 11/2006 |
| WO | WO 07/021834 | 2/2007 |
| WO | WO 07/103562 | 9/2007 |
| WO | WO 07/136783 | 11/2007 |
| WO | WO 08/15257 | 2/2008 |
| WO | WO 08/068756 | 6/2008 |
| WO | WO 08/088716 | 7/2008 |
| WO | WO 09/120764 | 10/2009 |
| WO | WO 09/126629 | 10/2009 |
| WO | WO 09/140268 | 11/2009 |
| WO | WO 10/011699 | 1/2010 |
| WO | WO 10/048151 | 4/2010 |
| WO | WO 12/027116 | 3/2012 |
| WO | WO 12/167095 | 12/2012 |
| WO | WO 13/088327 | 6/2013 |
| WO | WO 14/043527 | 3/2014 |
| WO | WO 15/77599 | 5/2015 |

OTHER PUBLICATIONS

Bonow et al., "ACC/AHA 2006 Guidelines for the Management of Patients with Valvular Heart Disease," J. American College of Cardiology, 48(3):e1-148 (2006).
Boston Scientific, "Device Details." Retrieved from the Internet: http://bostonscientific.com/med_specialty/deviceDetail.jsp [retrieved on Aug. 31, 2006], 1 page.
Braunberger et al., "Very Long-Term Results (More Than 20 years) of Valve Repair with Carpentier's Techniques in Nonrheumatic Mitral Valve Insufficiency," Circulation, 104:I8-I11 (2001).
Braunwald et al., "Conservative Management of tricuspid Regurgitation in Patients Undergoing Mitral Valve Replacement," Circulation, XXXV and XXXVI:I63-I69 (1967).
Carpentier et al., "Surgical Management of Acquired Tricuspid Valve Disease," J. Thoracic and Cardiovascular Surgery, 67(1):53-65 (1974).
Center for Devices and Radiological Health, U.S. Dept. of Health and Human Services Food and Drug Administration "Guidance for Annuloplasty Rings 510(k) Submissions; Final Guidance for Industry and FDA Staff," 1-15 (2001).
Cosgrove et al., "Mitral Valvuloplasty," Curro. Probl. Cardiol., 359-405 (1989).
Dreyfus et al., "Secondary Tricuspid Regurgitation or Dilatation: Which Should Be the Criteria for Surgical Repair?," Ann. Thorac. Surg., 79:127-32 (2005).
Google Images, Recurved Hooks. Retrieved from the Internet: www.implementology.org.pf and personal.cityu.edu.hk [retrieved on Dec. 14, 2006], 1 page.
Leung et al., "Barbed, Bi-directional Surgical Sutures: In Vivo Strength and Histopathology Evaluations," Society for Biomaterials 28th Annual Meeting Transactions, #724 (2003) 1 p.
Magovern et al., "Sutureless Artificial Heart Valves," Circulation, 27:784-788 (1963).
McCarthy et al., "Tricuspid Valve Repair: Durability and Risk Factors for Failure," J. Thoracic and Cardiovascular Surgery, 127:674-85 (2004).
Nath et al., "Impact of Tricuspid Regurgitation on Long-Term Survival," J. American College of Cardiology, 43(3):405-409 (2004).
Navia et al., "Surgical Management of Secondary Tricuspid Valve Regurgitation: Anulus, Commissure, or Leaflet Procedure?," Abstract presented at American Association for Thoracic Surgery Annual Meeting (2009).
Rogers et al., "The Tricuspid Valve: Current Perspective and Evolving Management of Tricuspid Regurgitation," Circulation, 119:2718-2725 (2009).
Sagie et al., "Determinants of Functional Tricuspid Regurgitation in Incomplete Tricuspid Valve Closure: Doppler Color Flow Study of 109 Patients," J. American College of Cardiology, 24:446-53 (1994).
Savage et al., "Use of Mitral Valve Repair: Analysis of Contemporary United States Experience Reported to the Society of Thoracic Surgeons National Cardiac Database," Ann. Thorac Surg., 75:820-825 (2003).
Shiran et al., "Tricuspid Regurgitation in Mitral Valve Disease," J. American College of Cardiology, 53(5):401-408 (2009).
Song et al., "Factors Associated with Development of Late Significant Tricuspid Regurgitation after Successful Left-Sided Valve Surgery," Heart, 95:931-936 (2009).
Tang et al., "Tricuspid Valve Repair with an Annuloplasty Ring Results in Improved Long-Term Outcomes," Circulation, 114:1577-1581 (2006).
Thompson, "Percutaneous Heart Valve Technology: The Mitral Challenge," Medtech Insight, 11(2):38-52 (2009).
Zlotnick et al., "A Perfectly Functioning Magovem-Cromie Sutureless Prosthetic Aortic Valve 42 Years After Implantation," Circulation, 117:e1-e2 (2008).
International Search Report and Written Opinion; Application No. PCT/US2013/059751; pp. 8 dated Dec. 11, 2013.
Extended European Search Report dated Jun. 13, 2016 in European patent application No. 13837432.7.
International Search Report and Written Opinion dated May 26, 2017 for PCT/US2017/016284.
International Search Report dated Oct. 8, 2015 for PCT/US2015/040622.
International Search Report dated Jul. 1, 2008 for PCT/US2008/050224.
International Search Report dated Jul. 13, 2010 for PCT/US2010/027943.
International Search Report dated Sep. 22, 2011 for PCT/US2011/039022.
International Search Report dated Dec. 7, 2011 for PCT/US2011/047345.
International Search Report dated Jul. 21, 2014 for PCT/US2014/026333.
International Search Report dated May 5, 2016 for PCT/US2016/017866.
International Search Report dated Apr. 19, 2017 for PCT/US16/062107.

* cited by examiner

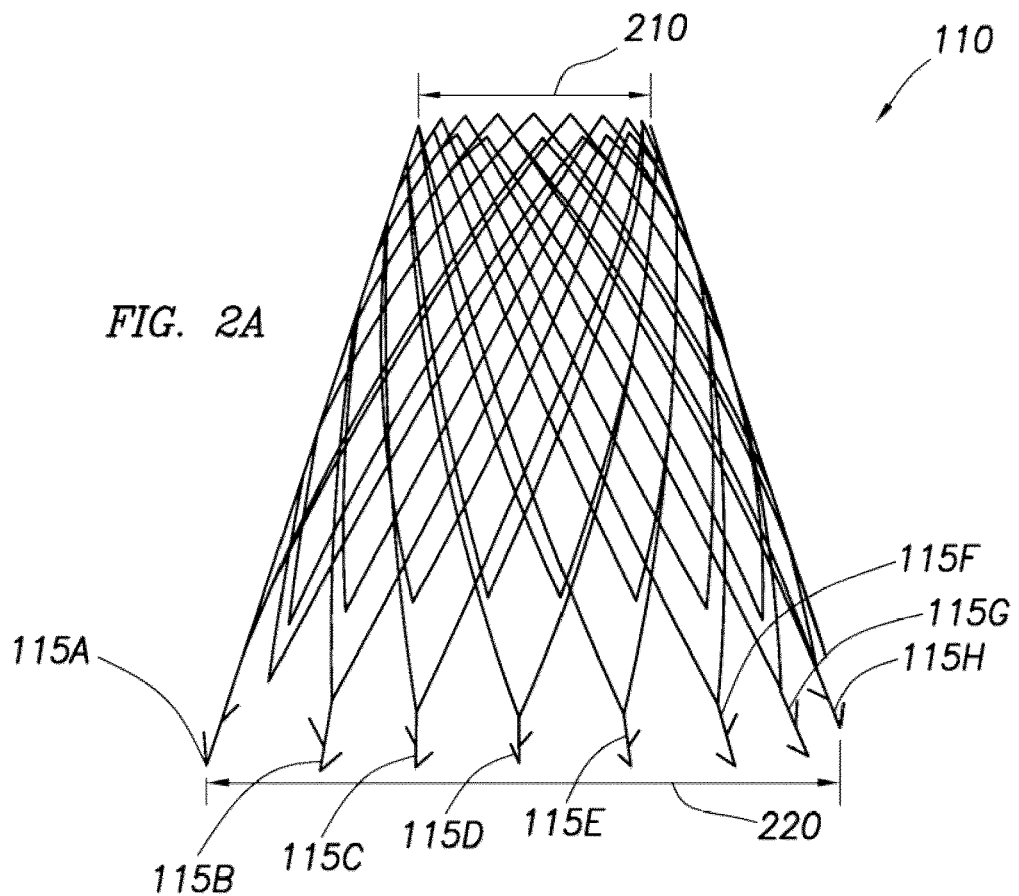
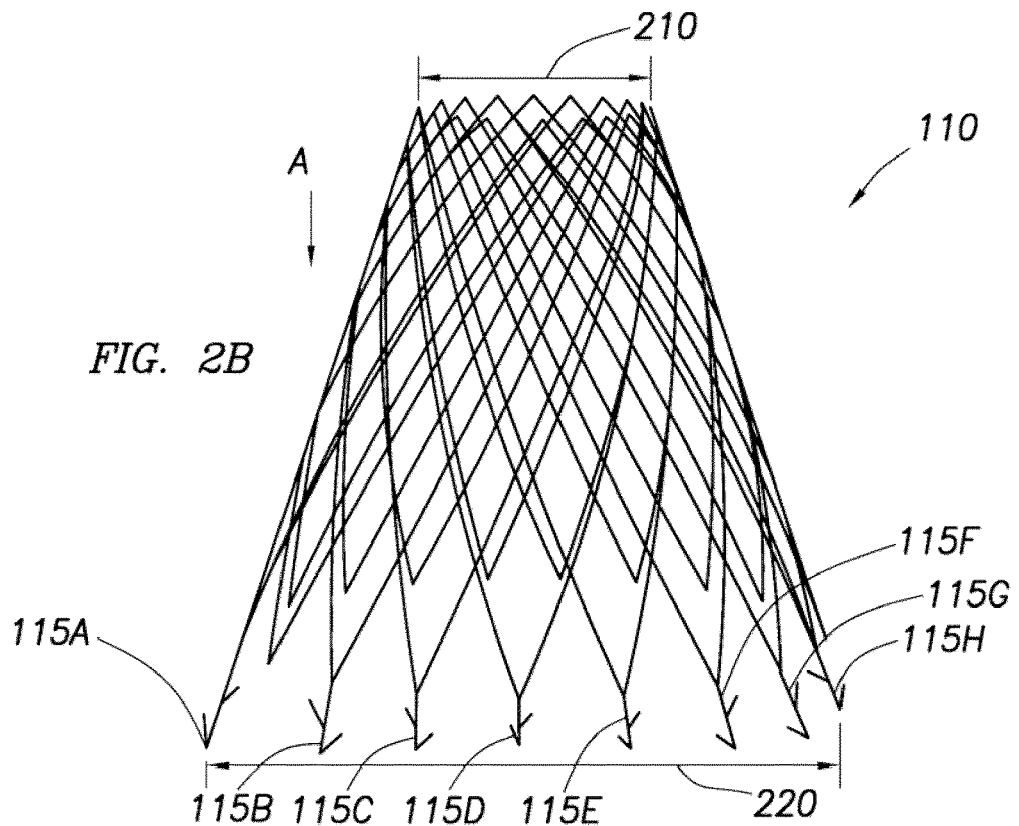

MITRAL VALVE INVERSION PROSTHESES

CROSS REFERENCE TO RELATED APPLICATIONS

This application is a Continuation-in-Part Application of U.S. application Ser. No. 14/427,909, filed on Mar. 12, 2015, which is a U.S. National Phase Application of PCT International Application Number PCT/US2013/059751, filed on Sep. 13, 2013, designating the United States of America and published in the English language, which is an International Application of and claims the benefit of priority to U.S. Provisional Application No. 61/700,989, filed on Sep. 14, 2012. Each of the above-referenced applications are hereby expressly incorporated by reference in their entireties for all purposes and form a part of this specification. Any and all priority claims identified in the Application Data Sheet, or any correction thereto, are hereby incorporated by reference under 37 C.F.R. § 1.57.

BACKGROUND

A. Field

This disclosure relates generally to cardiac treatment devices and techniques, and in particular, to methods and devices for repair of mitral valve defects such as mitral valve regurgitation.

B. Background of Related Art

The mitral valve is one of four heart valves that direct blood through the two sides of the heart. The mitral valve itself consists of two leaflets, an anterior leaflet and a posterior leaflet, each of which are passive in that the leaflets open and close in response to pressure placed on the leaflets by the pumping of the heart.

Among the problems that can develop or occur with respect to the mitral valve is mitral valve regurgitation (MR), in which the mitral valve leaflets become unable to close properly, thus causing leakage of the mitral valve. Severe mitral regurgitation is a serious problem that, if left untreated, can adversely affect cardiac function and thus compromise a patient's quality of life and life span.

Currently, mitral regurgitation is diagnosed by many indicators, and the mechanism of mitral regurgitation can be accurately visualized by trans-esophageal echocardiography or fluoroscopy with dye injection. The most prevalent and widely accepted current technique to correct mitral regurgitation is to repair the mitral valve via open-heart surgery while a patient's heart is stopped and the patient is on cardiopulmonary bypass, a highly invasive procedure that has inherent risks.

SUMMARY

In one aspect, a method is described comprising inserting an implant proximate a mitral valve, the implant comprising a tubular body and a plurality of piercing members, the tubular body comprising an upper (i.e. proximal) diameter and a lower (i.e. distal) diameter. The method also includes engaging tissue proximate the mitral valve by the plurality of piercing members and transitioning the tubular body from a first structural configuration to a second structural configuration by application of an expansive force to the tubular body proximate the upper diameter, the first structural configuration having the upper diameter smaller than the lower diameter and the second structural configuration having the upper diameter larger than the lower diameter.

In another aspect, an implant is described comprising a tubular body comprising an upper diameter and a lower diameter, the tubular body having a first structural configuration in which the upper diameter is smaller than the lower diameter and a second structural configuration in which the upper diameter is larger than the lower diameter, the tubular body configured to transition from the first structural configuration to the second structural configuration by application of an expansive force to the tubular body proximate the upper diameter. The implant also comprises a plurality of piercing members connected to the tubular body and proximate the lower diameter to engage tissue proximate a mitral valve.

In another aspect, a system is described comprising a guide wire, a sheath over the guide wire, and an implant for delivery to a body by traveling through the sheath and along the guide wire. The implant comprises a tubular body comprising an upper diameter and a lower diameter, the tubular body having a first structural configuration in which the upper diameter is smaller than the lower diameter and a second structural configuration in which the upper diameter is larger than the lower diameter, the tubular body configured to transition from the first structural configuration to the second structural configuration by application of an expansive force to the tubular body proximate the upper diameter. The implant also comprises a plurality of barbs connected to the tubular body and proximate the lower diameter to penetrate tissue proximate a mitral valve.

In another aspect, a delivery system for delivering an implant within the heart for reducing the size of a heart valve annulus is described. The delivery system comprises a plurality of rotatable drivers and the implant. The plurality of rotatable drivers is configured to extend through one or more lumens of the delivery system. The implant is configured for delivery within the heart by traveling through the one or more lumens of the delivery system. The implant comprises a tubular body and a plurality of helical anchors. The tubular body comprises a frame defining a proximal diameter and a distal diameter. The tubular body has a first structural configuration in which the proximal diameter is smaller than the distal diameter and a second structural configuration in which the proximal diameter is larger than the distal diameter. The plurality of helical anchors are connected to the tubular body proximate the distal diameter of the frame. The plurality of helical anchors are configured to be rotated by the rotatable driver to advance the plurality of helical anchors distally relative to the frame and penetrate the heart valve annulus.

In some embodiments of the delivery system, the implant may further comprise a series of distal apices and a series of holes. The series of distal apices may be formed by the frame proximate the distal diameter. The series of holes may be in each of the distal apices and are sized and spaced to receive therethrough a corresponding helical anchor for rotational engagement of the distal apex by the corresponding helical anchor. The plurality of rotatable drivers and the implant may be configured for transcatheter delivery of the implant to the heart. The delivery system may further comprise a delivery catheter comprising the one or more lumens of the delivery system. A distal end of the delivery catheter may be configured to advance through an opening in the femoral vein, through the femoral vein and into the right atrium of the heart, and through the septum of the heart into the left atrium. The delivery system may further comprise a location ring configured to be located on a side of the heart valve opposite the implant and to couple with the implant. The location ring may be separate from the implant and configured to be located on a side of the heart valve opposite the implant to assist in positioning the implant. The location ring may be configured to be removed from the heart after the implant is positioned and the plurality of helical anchors penetrate the heart valve annulus. The delivery system may comprise one lumen configured to receive therethorugh an intracardiac echo catheter for visualizing a position of the implant relative to the mitral valve annulus. The delivery system may further comprise the intracardiac echo catheter. The implant may further comprise an expandable tubular member coupled with a proximal end of the frame and configured to expand to increase the proximal diameter of the frame. The expandable tubular member may be integral with the frame.

In another aspect, an implant for reducing the size of a heart valve annulus is described. The implant comprises a tubular body and a plurality of helical anchors. The tubular body comprises a frame defining a proximal diameter and a distal diameter. The tubular body has a first structural configuration in which the proximal diameter is smaller than the distal diameter and a second structural configuration in which the proximal diameter is larger than the distal diameter. The plurality of helical anchors are connected to the tubular body proximate the distal diameter of the frame. Each of the plurality of helical anchors is configured to be rotated by a plurality of rotatable drivers through a series of holes in lower apices of the frame to advance the plurality of helical anchors distally relative to the frame and penetrate the heart valve annulus.

In some embodiments, the implant further comprises an expandable tubular member proximate a proximal end of the frame, wherein when force is applied to the expandable member, the expandable member expands and engages the proximal end of the frame causing the frame to invert from the first structural configuration to the second structural configuration. The expandable tubular member may be integral with the proximal end of the frame. The expandable tubular member may be a stent-like member positioned internally of the frame proximate the proximal diameter of the frame. The implant may be configured to be contracted to a delivery configuration for transcatheter delivery of the implant to the heart by a delivery system. The implant may further comprise an expandable tubular member coupled with a proximal end of the frame, wherein contracting the expandable tubular member for transcatheter delivery causes the proximal diameter of the frame to decrease relative to an unconstrained state, which causes the distal diameter of the frame to increase relative to the unconstrained state such that the proximal and distal diameters of the frame are approximately the same when delivered. The implant may further comprise angled segments of the frame forming distal apices of the frame proximate the distal diameter, and the series of holes in each of the distal apices may be sized and spaced to receive therethrough a corresponding helical anchor for rotational engagement of the distal apex by the corresponding helical anchor. The tubular body may be configured to transition from the first structural configuration to the second structural configuration by application of an expansive force to the tubular body proximate the proximal diameter.

BRIEF DESCRIPTION OF THE DRAWINGS

For a more complete understanding of the present disclosure and its features and advantages, reference is now made to the following description, taken in conjunction with the accompanying drawings, in which:

FIGS. 2A-2D illustrate an alternative example embodiment of an implant in accordance with the present disclosure;

DETAILED DESCRIPTION

The present disclosure relates to an implant including a tubular body and piercing members for reshaping a mitral valve suffering from mitral regurgitation. The implant may include two or more structural configurations. In a first structural configuration, an upper, i.e. proximal, diameter (away from the mitral valve) may be smaller than a lower, i.e. distal, diameter (proximate the mitral valve). In this first structural configuration, the piercing members of the implant may engage the tissue proximate the mitral valve, for example, the mitral valve annulus. The implant may then be transitioned from the first structural configuration to a second structural configuration in which the size of the upper diameter is larger than the lower diameter. This may be facilitated by an expansive force causing the upper diameter to expand, in turn causing the lower diameter to contract. As the lower diameter contracts, the penetrating members engaged with the tissue proximate the mitral valve may cause the mitral valve to also contract to a smaller diameter. This may allow the valve leaflets to close properly, addressing mitral regurgitation.

Figure 1A:
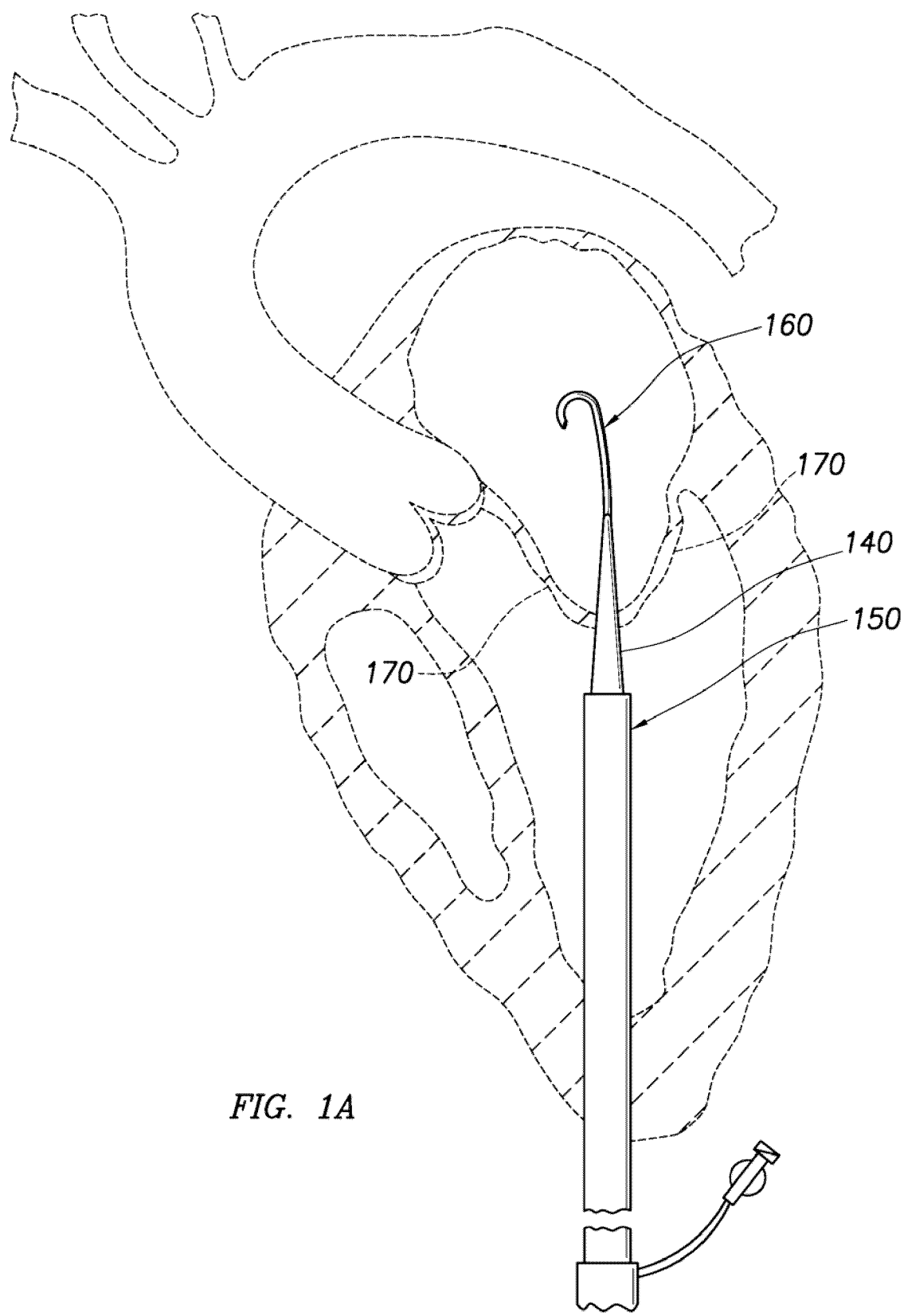
FIGS. 1A-1F illustrate an example embodiment of an implant in accordance with the present disclosure.

FIGS. 1A-F illustrate one embodiment of an implant. For example, as shown in FIG. 1A, in some embodiments, repair of a mitral valve may be achieved by a catheter system and catheterization procedure, wherein a catheter may be configured for percutaneous access to the mitral valve through the left ventricle. Access may be granted to the left ventricle through the apex of the heart where an incision may be made to insert a dilator and sheath 150 for access of a repair catheter 140. Sheath 150 may measure about six French to about thirty French and a closure device may be used in conjunction with the entry of this access catheter 140.

In one embodiment of the present disclosure, catheter 140 may include an extendable guide wire assembly 160, which may guide the system into position. Guide wire 160 may measure between 0.010 inches and 0.038 inches in diameter, and may be 0.035 inches in diameter. Catheter 140 or sheath 150 when accessed through the apex of the heart may measure about twenty to thirty centimeters in length.

Figure 1B:
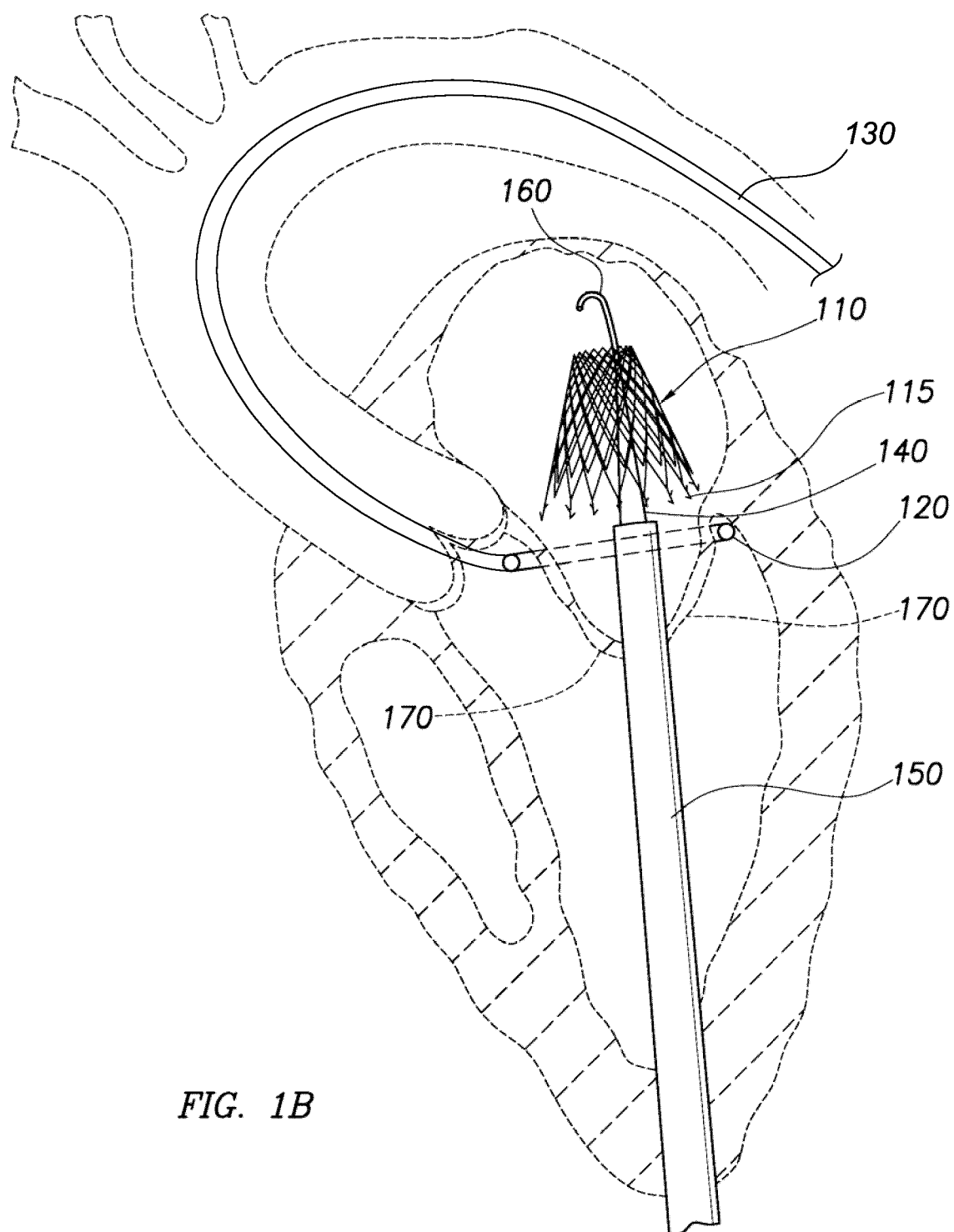

As shown in FIG. 1B, once access has been achieved, a delivery system may be introduced through sheath 150 along guide wire 160 with implant 110 for reducing the diameter of the mitral valve annulus. Catheter 140 may deliver implant 110 to resize the mitral valve to reduce the mitral valve cross sectional area or move the posterior leaflet back into position limiting or reducing mitral valve regurgitation.

Implant 110 may include a tubular body with portions of the tube removed similar to a stent structure where a portion of the material may be removed via laser cutting or other means to selectively cut portions of the tube away forming a radially-expandable tubular body. Implant 110 may be introduced in a collapsed structural configuration. This collapsed structural configuration may allow implant 110 to fit within sheath 150 to allow for a percutaneous procedure rather than an open-heart procedure. As shown in FIG. 1B, once implant 110 arrives in the left atrium, implant 110 may be expanded to a larger first structural configuration to engage tissue proximate the mitral valve, for example, the mitral valve annulus. In one embodiment, implant 110 may have a tubular shape with a free diameter of about twenty five to about thirty five millimeters in diameter, a height of about ten to about thirty millimeters, and a wall thickness of between about 0.005 inches and about 0.040 inches. Implant 110 may be constructed of a metallic material such as stainless steel, MP35N alloy, Nitinol or other implantable material.

In some embodiments, implant 110 may be tapered such that one end may be larger in diameter than the other end, appearing generally frustoconical in shape. The diameters of the ends may be approximately twenty five millimeters on the smaller end and approximately thirty five millimeters on the larger end. Implant 110 may also be non-circular where a portion of the implant may be elliptical or include a radial portion that is flat. This flat portion may be oriented toward the aortic valve and the circular portion may be positioned toward the posterior leaflet. To facilitate discussion of implant 110, an upper portion and lower portion may be described. The lower portion may refer to the end of implant 110 proximate mitral valve 170 while the upper portion may refer to the end of implant 110 free in the left atrium.

Implant 110 may include piercing members 115 proximate the lower portion of implant 110 proximate mitral valve 170 to engage with tissue proximate mitral valve 170, for example, the mitral valve annulus. Piercing members 115 may include barbs or hooks similar to fish hook barbs or other similar feature to resist withdrawal from tissue once pierced. Piercing members 115, barbs or hooks of the piercing members 115, or any combination thereof may pierce the tissue to engage with the tissue. Piercing members 115 may include a singular barb or hook, or a plurality of barbs or hooks per piercing member 115. Piercing members 115 may be immediately exposed or covered for delivery. They may number from one to fifty and may have a length of about four to twenty millimeters in length. They may have the same wall thickness as a wall of the tubular body of implant 110 or may differ with an increased or decreased thickness or taper in either direction to allow for mechanical integrity.

Piercing members 115 of implant 110 may be integral or attached to implant 110 as a secondary component glued, welded, or attached as an ancillary part. Piercing members 115 may also be laser cut into implant 110, and therefore attached to implant 110. The barbs or hooks may be fatigue resistant from fracture or separation from piercing members 115. For example, the barbs or hooks may have additional strength or wall thickness at the connection to piercing members 115. The barbs or hooks may also be attached with a hinged attachment allowing motion relative to the heart, but not longitudinally where the barbs or hooks may separate from piercing member 115.

The barbs or hooks of piercing member 115 may be active or passive meaning that the barbs or hooks may be activated with heat to bend or expose or mechanically formed through an external force to bend or expose. For example, each barb or hook may be sheathed inside a tube and removal of this tube may allow the barb or hook to be activated by, for example, body heat or some other activation factor, such that the barb or hook is exposed so as to engage the surrounding tissue. In a passive configuration, the barbs or hooks may be static in nature and either always exposed or exposed as soon as a covering is removed. The barbs or hooks may be hidden until deployment limiting the exposure during delivery and positioning and only exposed once positioning is finalized. The exposure may be completed as individual barbs or as multiples of barbs. In some embodiments, the covering is thus only a temporary covering.

As shown in FIG. 1B, in some embodiments, implant 110 may be positioned at the annulus of mitral valve 170 where the mitral valve hinge meets the left ventricle and the left atrium meets mitral valve 170. Positioning implant 110 at this location may be facilitated using a location ring 120. For example, location ring 120 may be positioned within the left ventricle, under mitral valve 170. A catheter to deliver location ring 120 may be placed in the left ventricle via the same access point through sheath 150. In some embodiments, a catheter 130 may extend through the aorta to deliver and/or remove the location ring 120. The catheter 130 as shown may extend through the aorta and through the aortic valve, and enter the left ventricle. In some embodiments, the location ring 120 may be delivered and/or removed from the apical entry point, as mentioned, or from trans-aortic entry via a femoral entry. In some embodiments, location ring 120 may comprise a metallic ring or coiled section, which may be viewed via fluoroscopy or echo guidance to confirm the location of location ring 120. This may allow confirmation of a positive location for implant 110 to be located with respect to the mitral valve annulus. In addition to the use of a location ring, other methods for determining a desired location to attach implant 110 may could include echo guidance, CT, fluoroscopy or MRI other imaging techniques to highlight the mitral valve hinge.

Figure 1C:
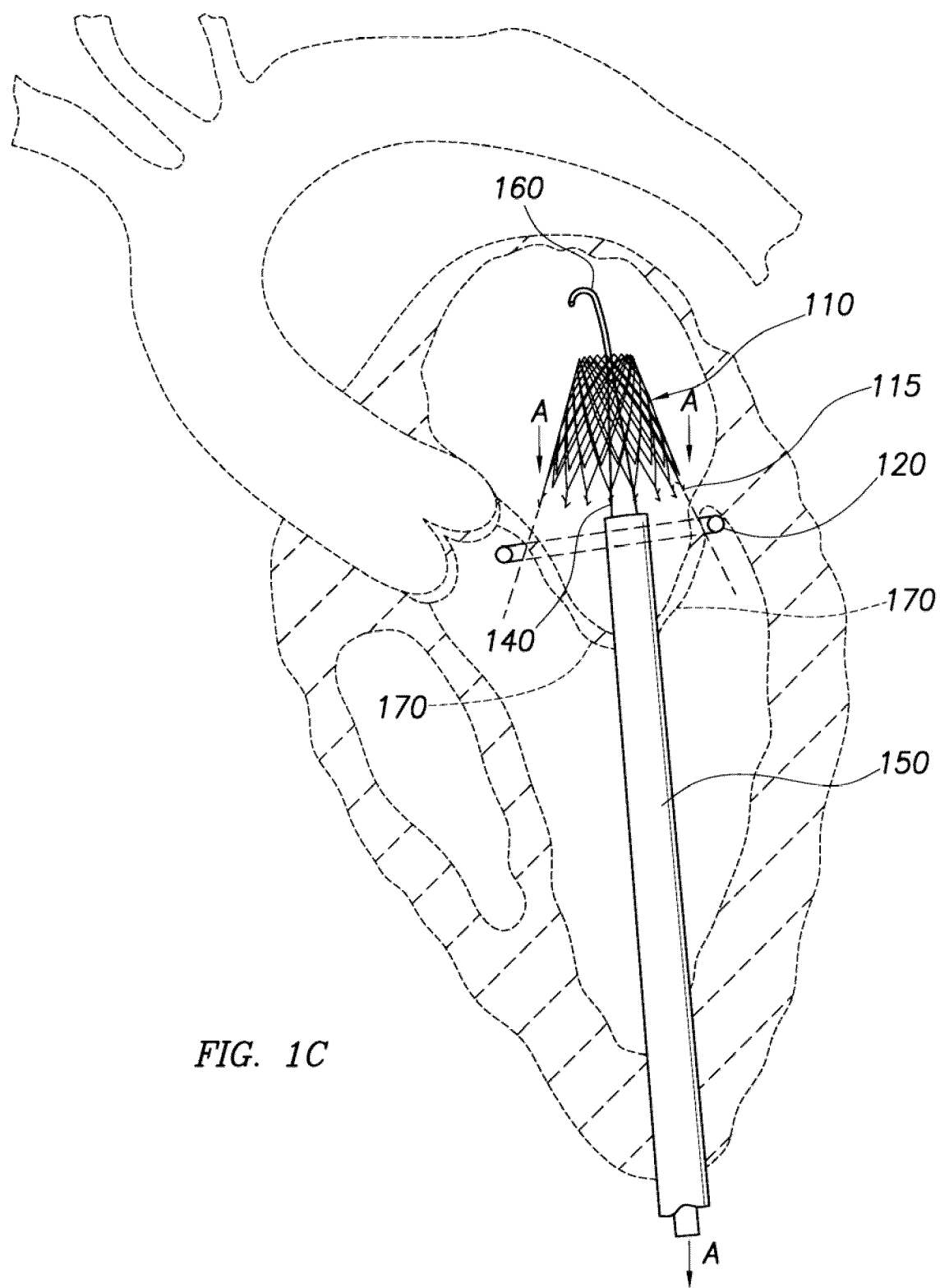

As shown in FIG. 1C, while in a first expanded structural configuration, and once a proper position has been achieved, implant 110 may have a downward force "A" applied to cause piercing members 115 to engage with and/or pierce the mitral valve annulus. This force may be applied by the delivery system itself, or may be applied by a secondary catheter that may be introduced for engaging piercing members 115 with the tissue proximate mitral valve 170.

Figure 1D:
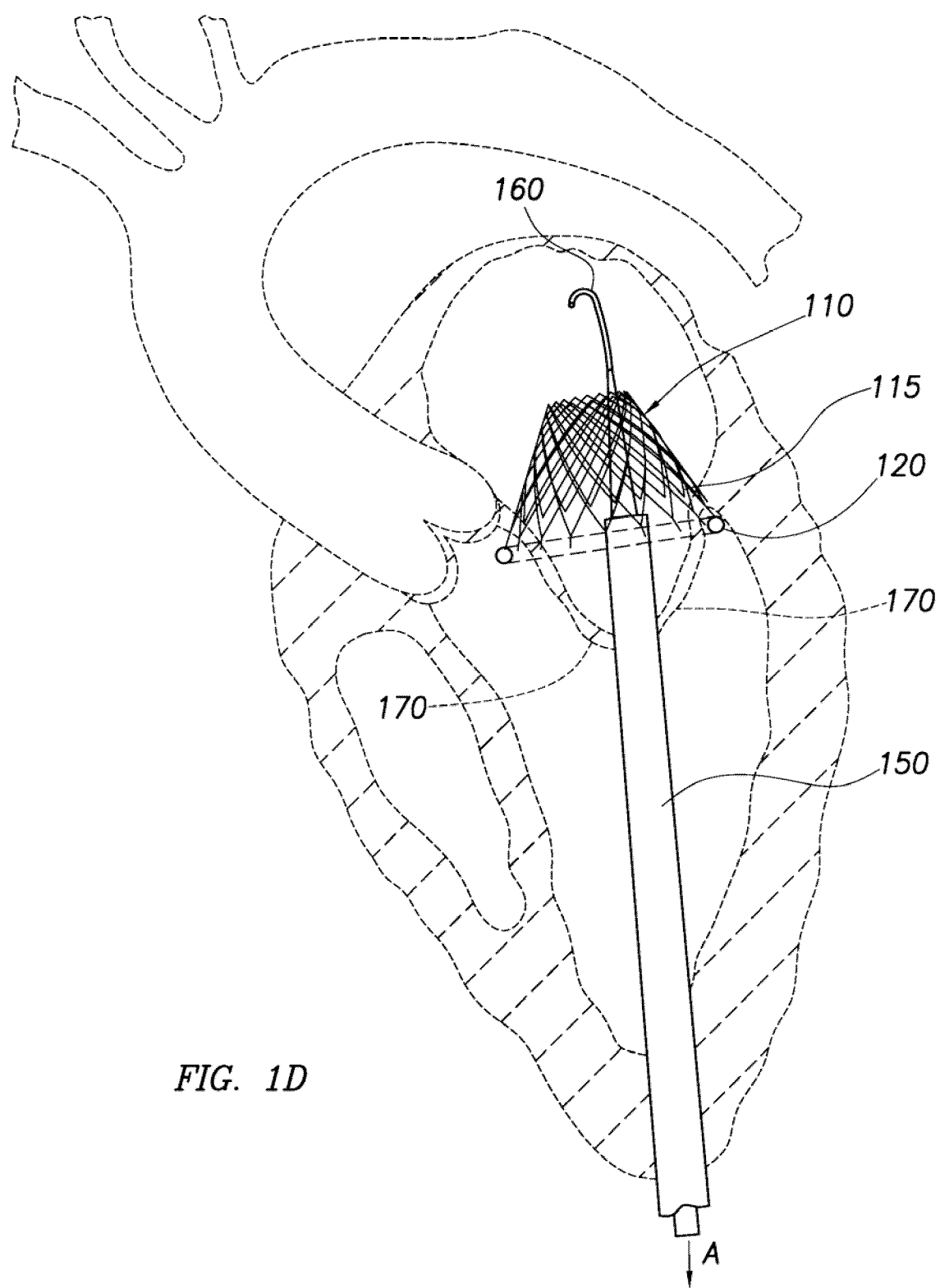

As shown in FIG. 1D, the location ring 120 may be used to locate the relative position of the implant 110 after anchoring the implant 110 to the annulus. For example, the location ring 120 may comprise a metallic ring or coiled section, which may be viewed via fluoroscopy or echo guidance to confirm the location of location ring 120 and implant 110. After confirmation of acceptable placement of the implant 110, or after inversion of the implant 110 as described below, the location ring 120 may then be removed. Thus, the location ring 120 may be temporary. The location ring 120 may thus be separate from the implant 110 and configured to be located on a side of the heart valve opposite the implant 110 to assist in positioning the implant 110. The location ring 120 may be configured to be removed from the heart after the implant 110 is positioned and the plurality of helical anchors penetrate the heart valve annulus. The location ring 120 may be removed by the same delivery system by which it was inserted, for example the delivery system shown in FIGS. 1A-1F, the catheter 130, etc.

In some embodiments, location ring 120 may also act as an anchor for implant 110. In such an embodiment, implant 110 above mitral valve 170 (i.e. in the left atrium side of mitral valve 170) may attach to location ring 120 below mitral valve 170 (i.e. in the left ventricle side of mitral valve 170). For example, the hooks or barbs of piercing members 115 may engage with location ring 120. This may be accomplished by a through suture, a barbed means, wrapping or clipping location ring 120 to implant 110. Magnetic forces may also hold location ring 120 and implant 110 together either temporarily or permanently. Alternatively, the hooks or barbs may also be attached to some other separate implant below mitral valve 170 in the left ventricle. This may be a wire, ring, or tee anchor to secure implant 110 to via wires, threads or mechanical means to attach through the tissue median. For convenience, this implant below mitral valve 170 may be referred to as location ring 120, even if not used in locating implant 110 proximate mitral valve 170.

In some embodiments, the shape of location ring 120 may be a circular cross section measuring about 0.010 inches to about 0.090 inches in diameter and may encircle the mitral annulus. The shape may also be non-circular, oval, biased to one axis or multi-axis to accommodate the multi-plane shape of mitral valve 170, which is more saddle shaped. It may also have a variable stiffness in different sections to accommodate tighter bends in the placement of location ring 120. Location ring 120 and or a delivery catheter may also be steerable to navigate the area under mitral valve 170 for ease of placement. Utilizing push pull wires to compress or load portions of the catheter or location ring 120 to predictably bend and orient the catheter or location ring 120 may allow a user to access difficult anatomical features en route to and around mitral valve 170.

Figure 1E:
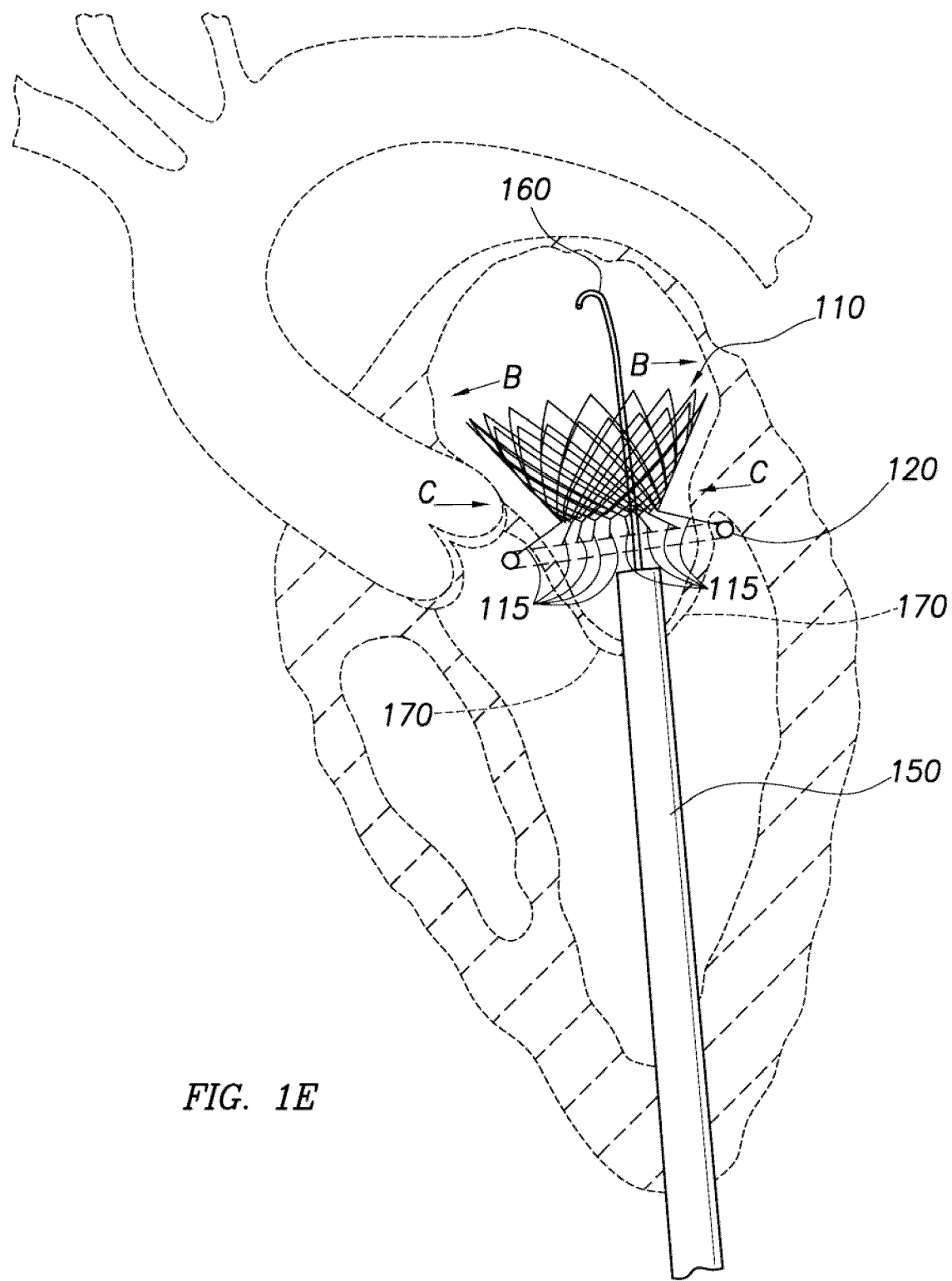

As shown in FIG. 1E, once piercing members 115 have engaged the tissue proximate mitral valve 170, for example, the mitral valve annulus, an expansive force "B" may be applied to the upper portion of implant 110. By applying expansive force "B" to implant 110, a reactive reducing force "C" may also be produced at the lower portion of implant 110. As the diameter of the lower portion is decreased from reactive reducing force "C," the diameter of mitral valve 170 is also reduced due to the attachment of implant 110 to the tissue around mitral valve 170. For example, once a sufficient reducing force "C" has been generated to reshape mitral valve 170 to a desired size, implant 110 may be left in a final position in which the size change of mitral valve 170 may be maintained. This may be a second structural configuration.

Figure 1F:
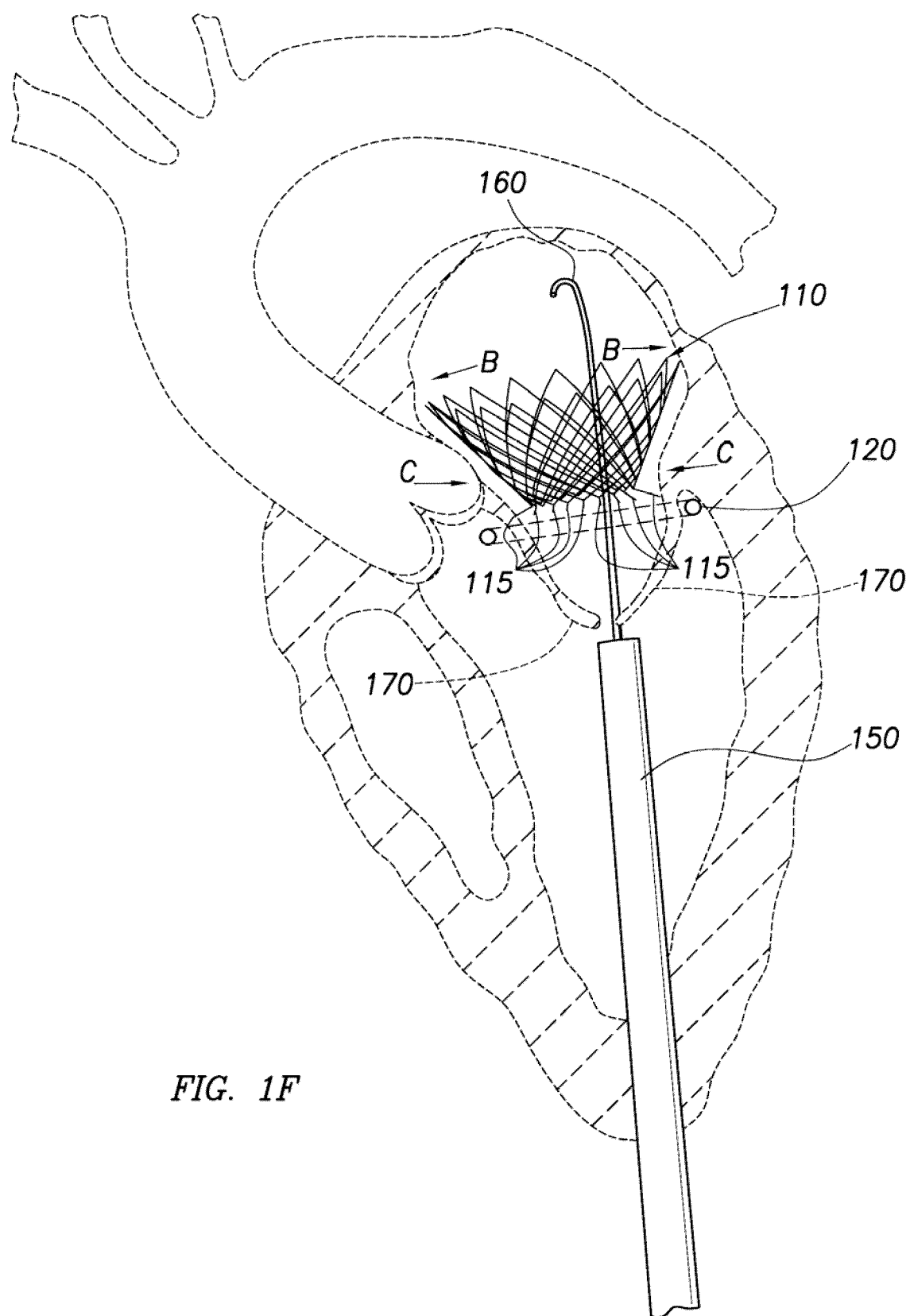

As shown in FIG. 1F, in some embodiments, piercing members 115 may engage the tissue proximate mitral valve 170 but not engage location ring 120. In such an embodiment, the barbs or hooks of piercing members 115 may bind, engage with, and/or resist withdrawal from tissue proximate mitral valve 170 in a manner sufficient to keep implant 110 attached to the tissue proximate mitral valve 170. Additionally, the binding, engaging, and/or resisting withdrawal may be sufficient to decrease the surface area of mitral valve 170 as expansive force "B" and reactive reducing force "C" are applied. In such an embodiment, location ring 120 may or may not be used to facilitate placing implant 110 at a positive location proximate mitral valve 170. In some embodiments, as described, the location ring 120 may not couple with the implant 110 but may be used to facilitate positioning of the implant 110, such as by temporarily positioning the location ring 120, etc. A positive location for implant 110 may be one in which implant 110 is able to engage tissue proximate mitral valve 170 without impairing the function of mitral valve 170 and further implant 110 may be used to decrease the surface area of mitral valve 170 as expansive force "B" and reactive reducing force "C" are applied.

Figure 2C:
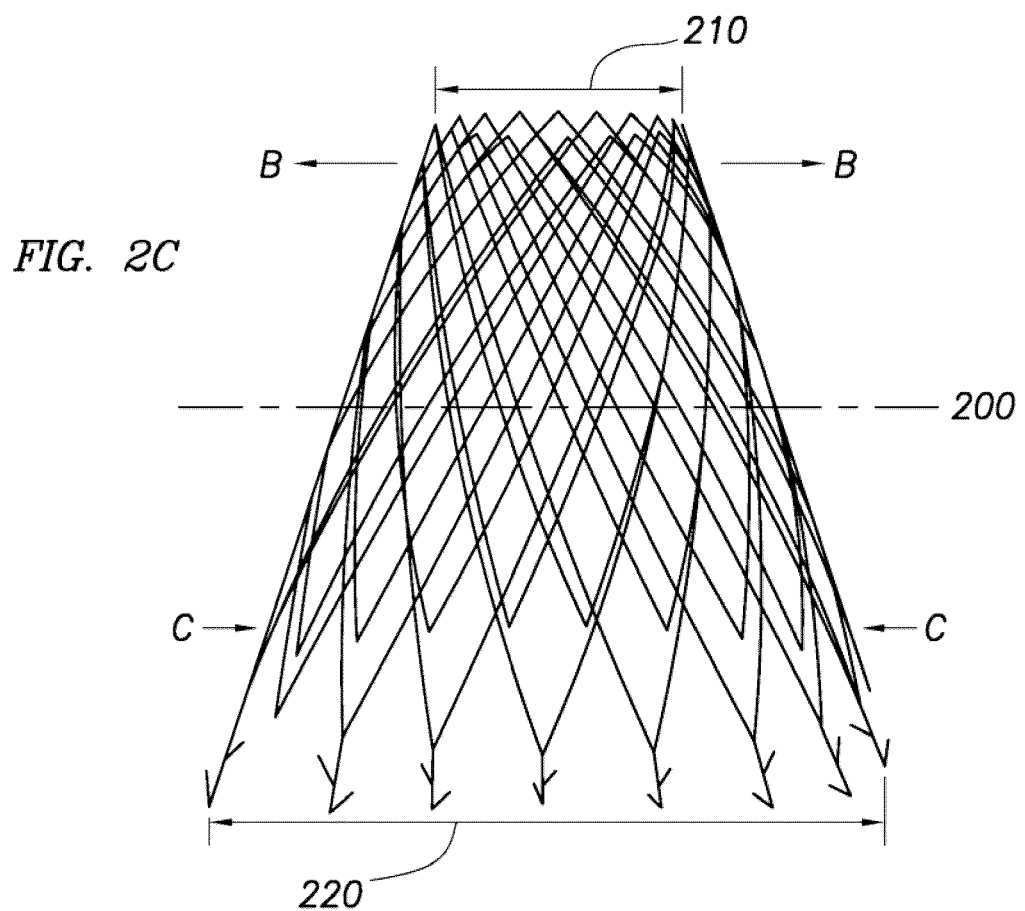

FIGS. 2A-2D illustrate an example of implant 110 in accordance with the present disclosure. As shown in FIG. 2A, implant 110 may be made of a metal and cut to form a mesh, a cage, or series of repeating units to allow variations in diameter. For example, implant 110 may include a tubular body of repeating squares, diamonds, hexagons, or any other shape allowing a variation in diameter of implant 110. In first structural configuration as shown in FIG. 2A, implant 110 may have the larger diameter portion initially oriented toward mitral valve 170 (the lower portion with lower diameter 220) and the smaller diameter may be oriented in the left atrium (the upper portion with upper diameter 210). The upper portion may be in free space in the left atrium and have a smaller diameter ready to be expanded in this first structural configuration.

The construction of implant 110 may include a tapered laser cut tube expanded to a predetermined diameter with wall thickness approximately 0.005 inches to approximately 0.050 inches and a strut thickness of approximately 0.010 inches to approximately 0.070 inches and an expanded diameter of approximately 1.00 inch. If the implant is tapered, the large diameter may measure about thirty five millimeters in diameter and the smaller diameter may measure about twenty five millimeters in diameter. In the first structural configuration, the lower portion (i.e. the larger diameter section) may have penetrating members 115 to engage the mitral annulus and hold implant 110 in position during annuls reduction and remain as a permanent implant.

As shown in FIG. 2B, downward force "A" may be applied to implant 110. In some embodiments, piercing members 115A-H may be driven to engage the tissue one at a time. For example, a linear force may drive the hooks or barbs of piercing member 115A into the tissue by pushing at the top of implant 110 above piercing member 115A, thus transmitting a force through to the piercing member 115A, driving it into the tissue. The delivery system or catheter applying the force may then be rotated and actuated again to engage another piercing member 115, for example adjacent piercing member 115B. Once piercing member 115B has been engaged with the tissue, this may be repeated until all piercing members 115 have been engaged with the tissue. Alternatively, in some embodiments, force "A" may be sufficient to engage multiple piercing members 115 at once, rather than engaging only a single piercing member 115 at a time. In some embodiments, all of piercing members 115 may be engaged at once.

Figure 2D:
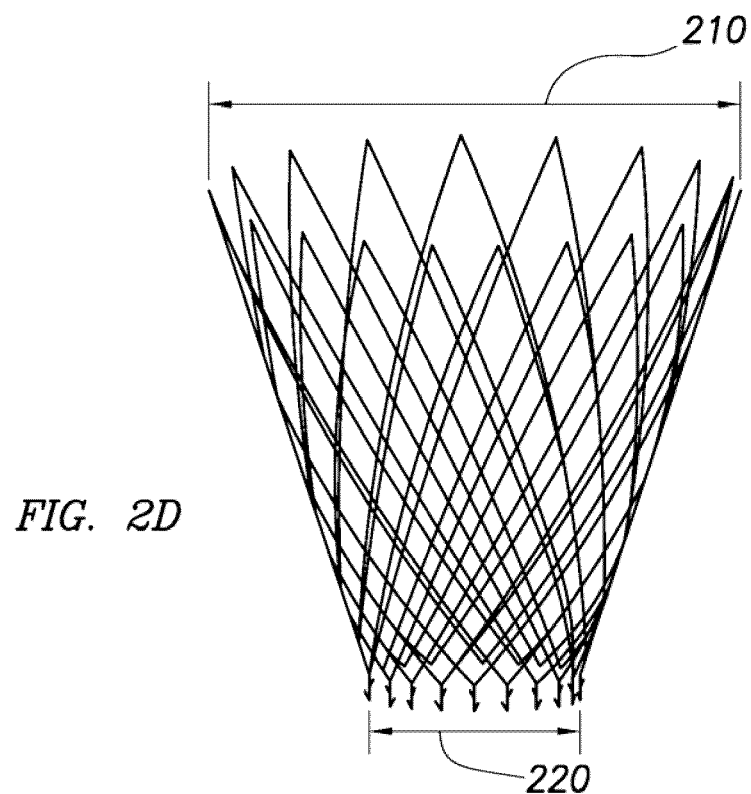

As shown in FIG. 2C, implant 110 may be in a first structural configuration in which upper diameter 210 may be smaller than lower diameter 220. An expansive force "B" may be applied to the upper portion of implant 110. As the expansive force "B" is applied such that the upper diameter 210 is increased, the lower diameter 220 may be decreased due to a reactive reductive force "C" which is generated. A wall of the tubular body of implant 110 may act as a beam in deflection where the upper portion of implant 110, when deflected (e.g. expanded), may cause the lower portion of implant 110 to bend (e.g. contract). This may facilitate the transition from this first structural configuration to a second structural configuration. The lower diameter 220 may be proximate piercing members 115, which are engaged with the mitral valve annulus. Thus, as lower diameter 220 becomes smaller, the diameter of mitral valve 170 becomes smaller. The expansive force "B" may be applied via balloon dilation, mechanical expansion or other means to increase upper diameter 210, thus reducing lower diameter 220. This may effectively invert implant 110's dimensions about axis 200, which may be referred to as an axis of inversion or axis of reflection. In some embodiments, the diameter of implant 110 at axis 200 may remain approximately uniform in a first structural configuration, transitioning between structural configurations, and a second structural configuration. As shown in FIG. 2D, the application of expansive force "B" and thus reactive reducing force "C" may result in implant 110 with upper diameter 210 having a larger length and lower diameter 220 having a shorter length. This may in turn reduce barb-engaged mitral valve 170 to a smaller annulus cross-sectional area, lessening the mitral regurgitation. The structural configuration shown in FIG. 2B may be the second structural configuration of implant 110 in which mitral valve 170 has been reduced in annulus cross-sectional area. Additionally, this second structural configuration may be a final structural configuration that may maintain the size change of mitral valve 170.

Figure 3A:
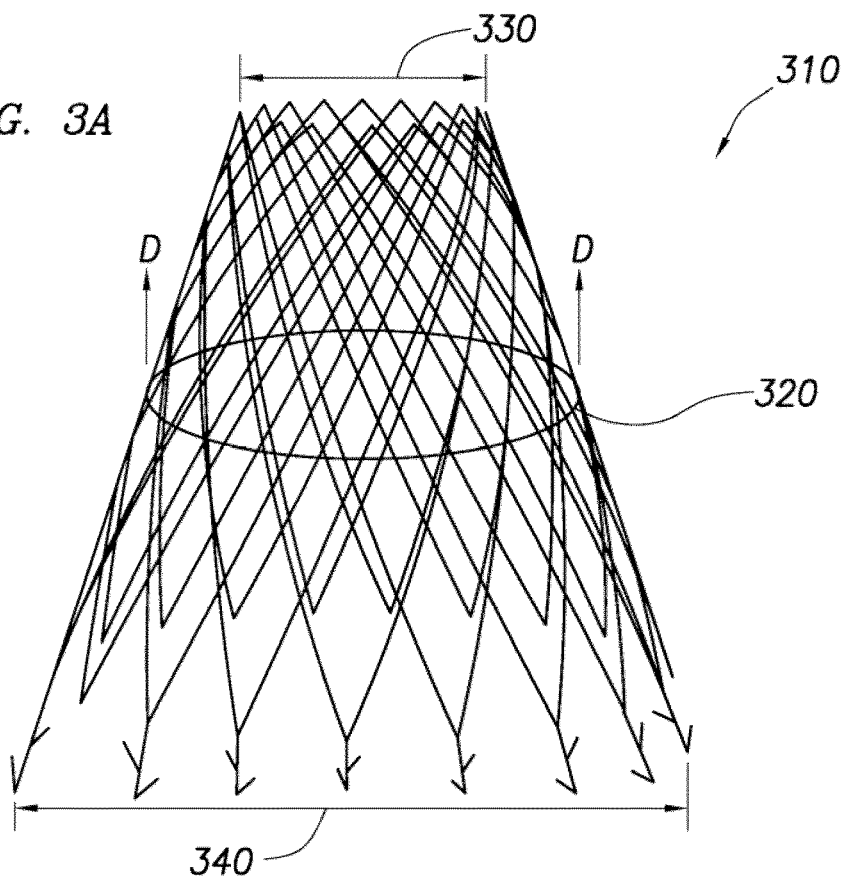
FIGS. 3A-3B illustrate a further alternative example embodiment of an implant in accordance with the present disclosure.
Figure 3B:
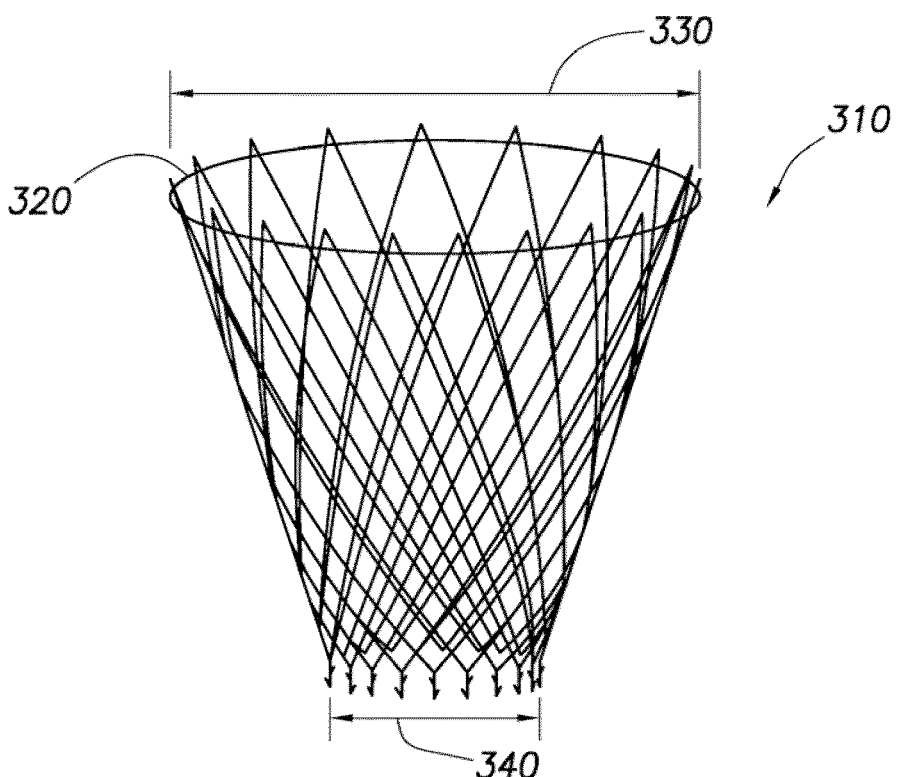

As shown in FIGS. 3A and 3B, an alternative method for applying an expansive force to implant 310 may be the deployment of a ring 320 within implant 310. FIG. 3A illustrates implant 310 in a first structural configuration and FIG. 3B illustrates implant 310 in a second structural configuration. The ring 320 may be formed of a shape memory material, such as nitinol. The ring 320 may be collapsed into a delivery catheter for delivery therethrough to the heart and ejected into or around the implant 310. In some embodiment, one or more releasable tethers may be attached to the ring 320. The releasable tethers may be pulled on to move the ring 320 and to release the tethers from the ring 320 after the ring 320 is in the desired location.

In some embodiments, a fixed ring 320 may be utilized. Fixed ring 320 may be moved vertically to expand the upper portion to increase upper, i.e. proximal, diameter 330, thus causing the lower portion to reduce lower, i.e. distal, diameter 340 along with the engaged tissue and mitral valve. For example, upward force "D" may be applied to ring 320. However, because of the frustoconical shape of implant 310, the upward force "D" may be translated to an expansive lateral force causing an increase in upper diameter 330. Ring 320 may lock into implant 310 by an interference fit or a mechanical stop built in ring 320 or implant 310, and may maintain implant 310 in the second structural configuration. In some embodiments, the fixed ring 320 may have a smaller diameter and initially be located at or near the upper diameter 330, thus restraining the upper diameter 330 and causing and/or maintaining the first structural configuration of the implant 310 shown in FIG. 3A. The fixed ring 320 may then be moved vertically downward as oriented toward the lower diameter 340, thereby allowing the upper diameter 330 to expand and increase in size and causing the lower diameter 340 to contract and reduce in size. The fixed ring 320 may then be located at or near the lower diameter 340 to cause and/or maintain the second structural configuration of the implant 310 shown in FIG. 3B.

Alternatively, an expandable ring 320 may be used rather than a fixed ring. Expandable ring 320 may be positioned within implant 310 and may be delivered and expanded by a catheter, for example using hydraulic or mechanical force to expand ring 320. Ring 320 may be introduced into implant 310's inner diameter where ring 320 may be tilted to allow for manipulation or positioning. Alternatively, ring 320 may be placed at a defined vertical position in implant 310 and ring 320 may be expanded, for example with mechanical or hydraulic force or an extension of the radial dimension. Ring 320 may also serve as a locking mechanism for implant 310 once the second structural configuration or the final position has been reached. The expansion and/or locking of ring 320 may be reversible in nature, thus undoing the expansion of the upper portion. Ring 320 may lock into implant 310, for example by an interference fit or a mechanical stop built in ring 320 and/or implant 310.

Figure 4A:
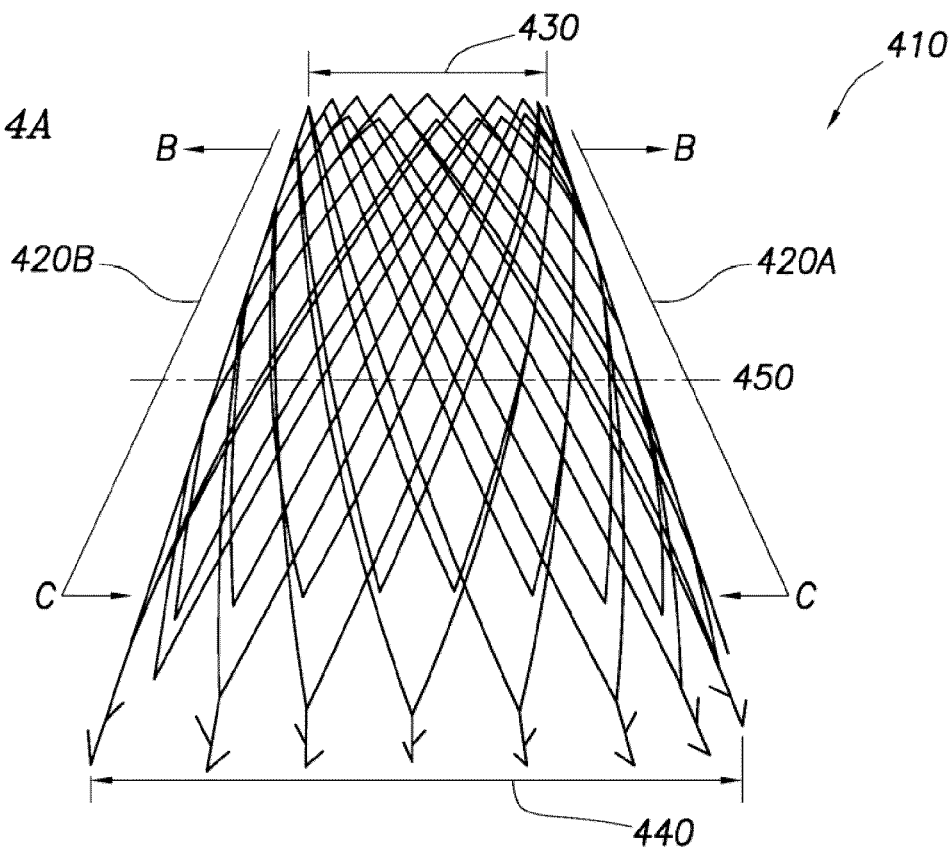
FIGS. 4A-4B illustrate an additional example embodiment of an implant in accordance with the present disclosure.
Figure 4B:
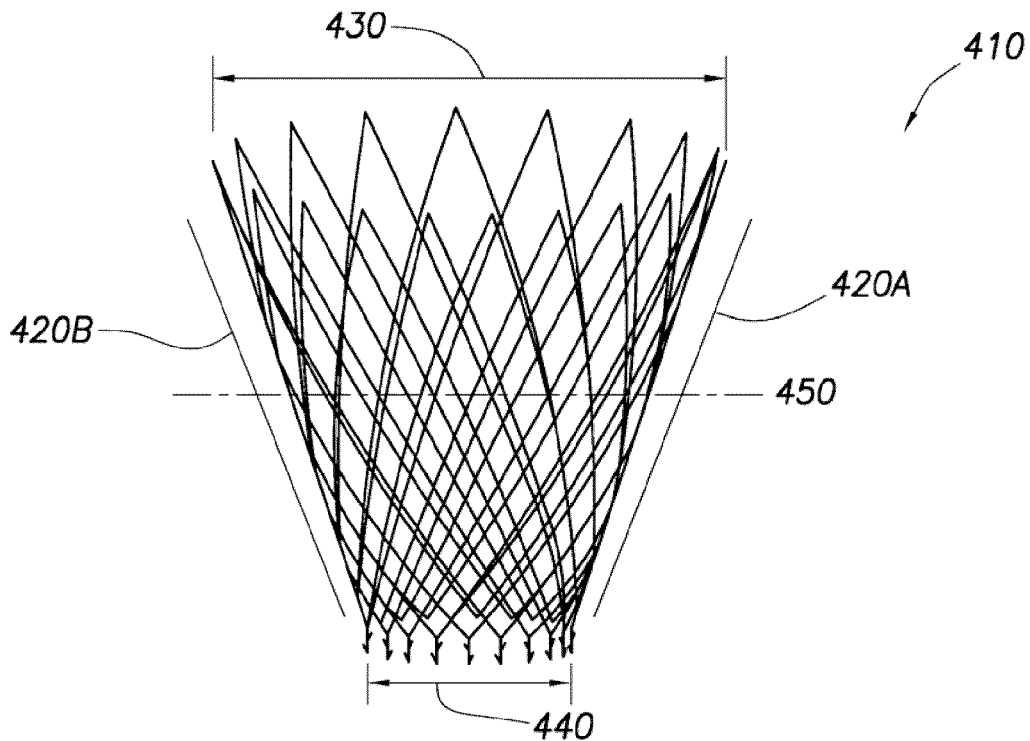

FIGS. 4A and 4B illustrate an additional embodiment of an implant 410 for reshaping mitral valve 170. FIG. 4A illustrates implant 410 in a first structural configuration and FIG. 4B illustrates implant 410 in a second structural configuration. As shown in FIG. 4A, in some embodiments, implant 410 may include one or more support beams 420 (for example, support beams 420A and 420B). Support beams 420 may facilitate the transition of expansive force "B" to the reductive force "C." For example, support beam 420 may operate as a beam in deflection about axis 450. Thus, as expansive force "B" is applied to the upper portion of implant 410, beams 420A and 420B may act as levers with axis 450 as the fulcrum or point of rotation, causing reductive force "C" to reduce lower diameter 440. As expansive force "B" is applied to increase upper diameter 430 and decrease lower diameter 440, implant 410 may transition from a first structural configuration shown in FIG. 4A to a second structural configuration shown in FIG. 4B. As described above, this may reduce the cross-sectional area of mitral valve 170.

Support beams 420A and 420B may be integrally formed with implant 410, for example, as a thicker portion of a wall of the tubular body of implant 410, or a specific alignment of repeating units or elements of the structure of the wall of the tubular body. Alternatively, support beams 420A and 420B may be an additional support component added to implant 410. For example, they may be glued, welded, or otherwise permanently affixed to implant 410.

Figure 5:
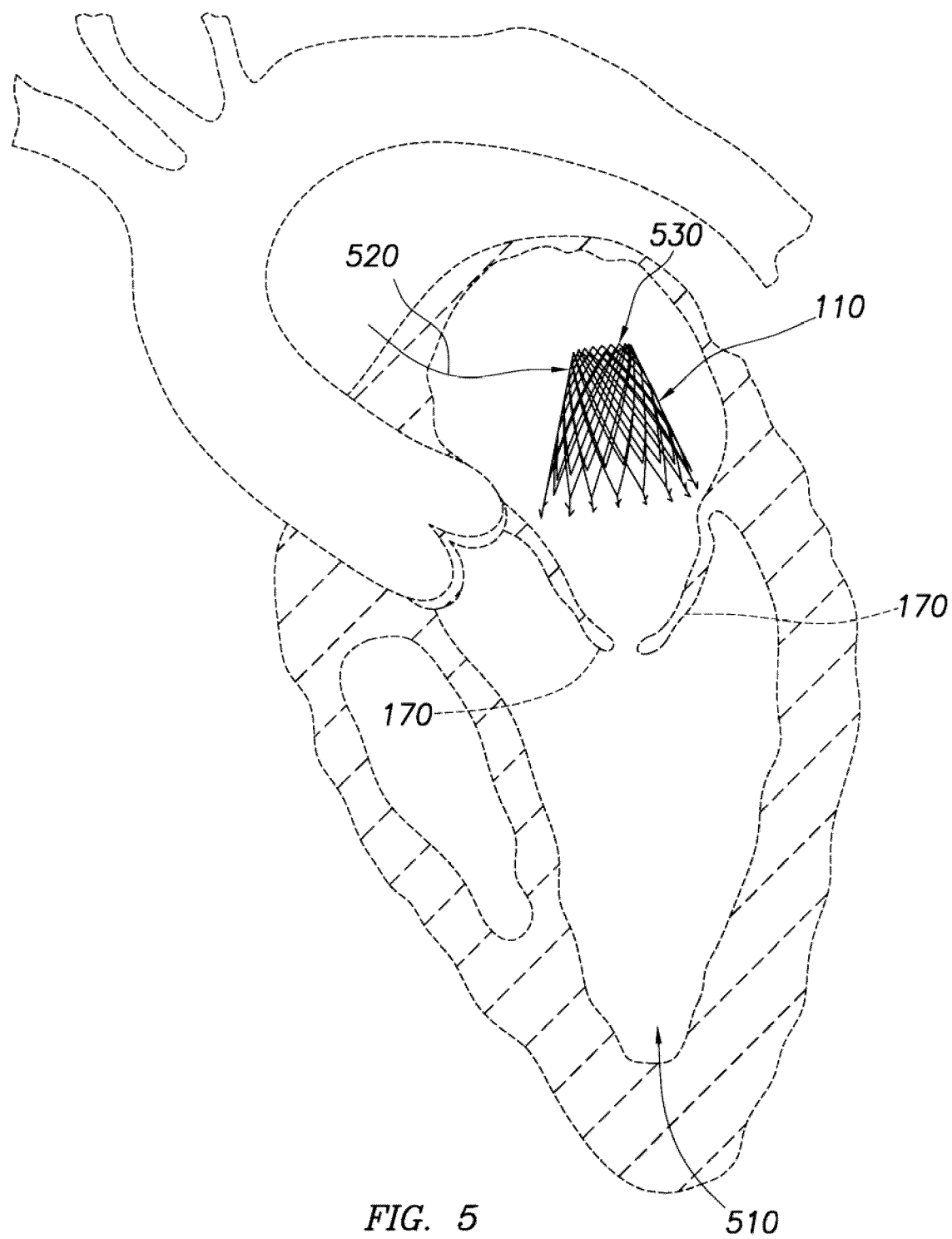
FIG. 5 illustrates examples of delivery routes of an implant, in accordance with the present disclosure.

As shown in FIG. 5, in addition to access to mitral valve 170 through the apex of the heart as shown by 510, access to mitral valve 170 may also be gained via the femoral artery as shown by 530, or via the femoral artery and through the aortic valve (for example, as described above with respect to delivery/removal of the location ring 120 through the aortic valve) or through the venous system and then via trans-septal puncture directly into the left atrium as shown by 520. When accessed via the femoral artery or trans-septally, a delivery catheter may measure about ninety to one hundred and fifty centimeters in length. The end of the catheter may be deflectable via deflection wires creating tension of bias to allow adjustments due to anatomical variations.

Figure 6:
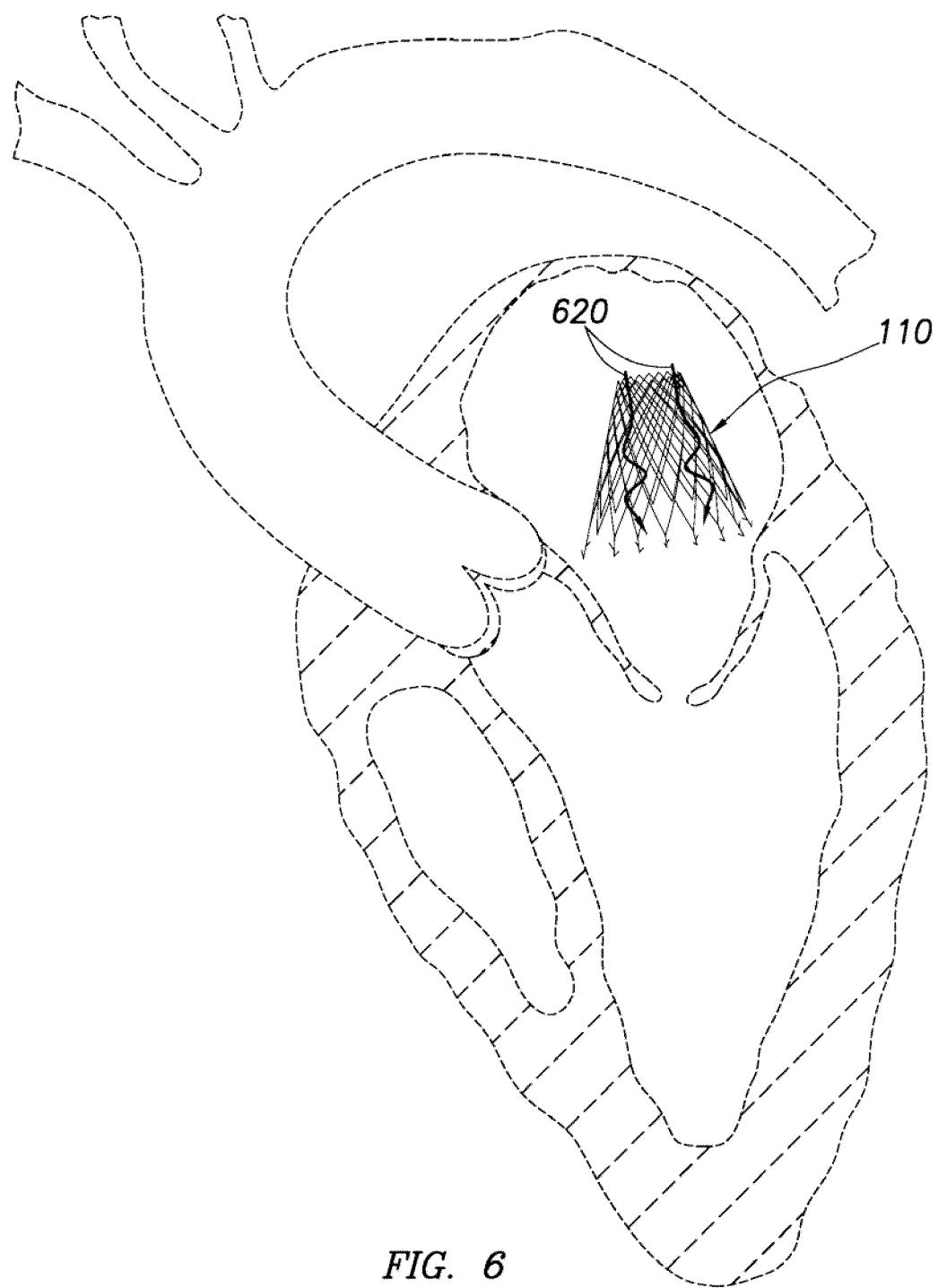
FIG. 6 illustrates an example embodiment of the present disclosure utilizing vibrations, in accordance with the present disclosure.

As shown in FIG. 6, vibration may be applied directly to penetrating members 115 to facilitate the barbs or hooks and/or penetrating members 115 penetrating the tissue. Low frequency vibration, ultrasonic, or Radio Frequency energy may allow a lower insertion force compared to the barb or hook's and/or penetrating members' normal penetration force. Coupling this energy source to implant 110 may allow transmission of small vibrations 620 to the tip of each barb or hook and/or penetrating member 115. Alternatively, each barb or hook and/or penetrating member 115 may have its own independent energy source allowing a variable pattern of frequency or energy around implant 110. Direct tissue contact of the energy element or a coupling to implant 110 may be used but there may be a decrease in efficiency by coupling vibration 620 thereto. The frequency of vibration 620 may be about ten to one hundred Hz (cycles per second) or may be about twenty Hz.

Figure 7:
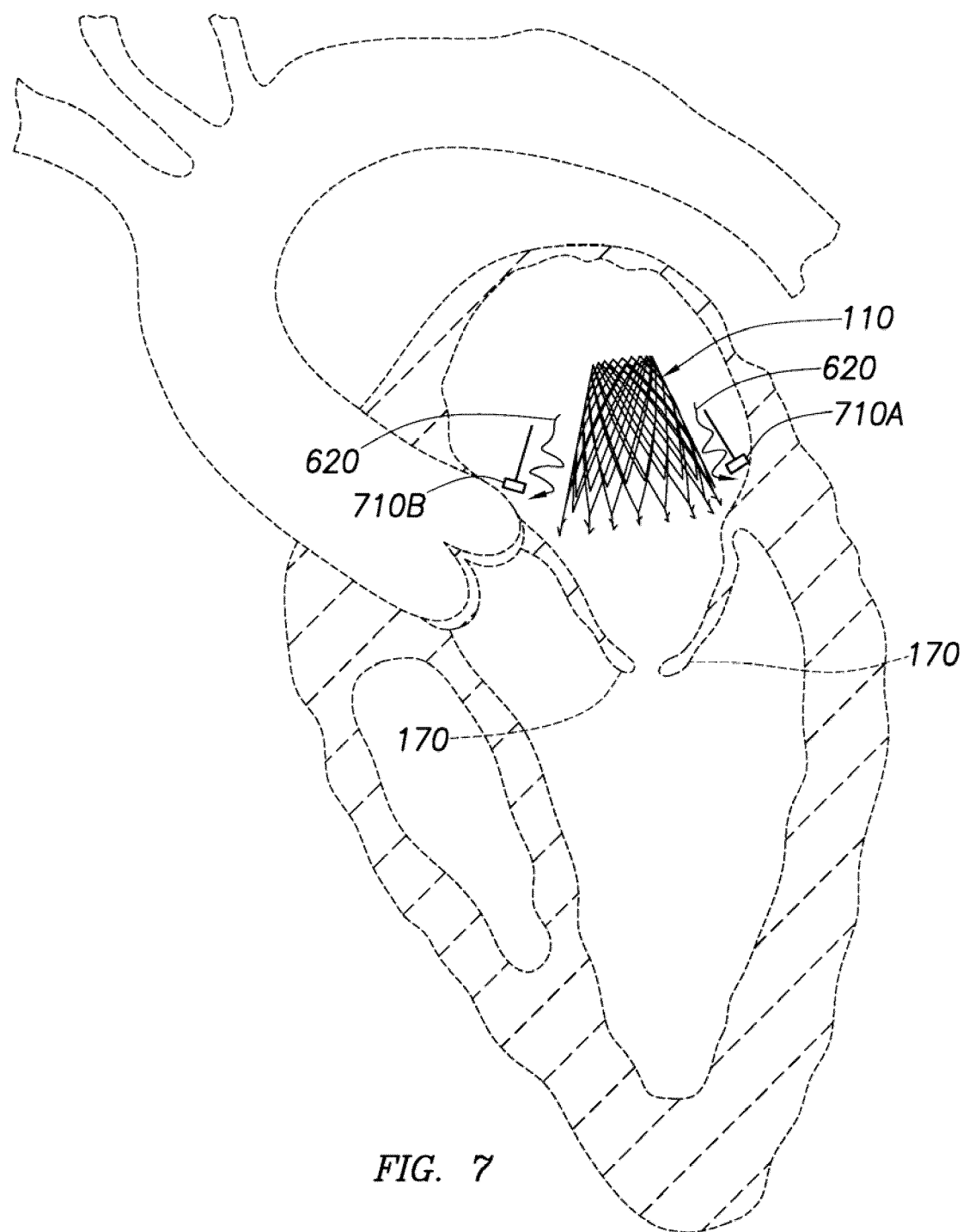
FIG. 7 illustrates an alternative example embodiment of the present disclosure utilizing vibrations, in accordance with the present disclosure.
Figure 8:
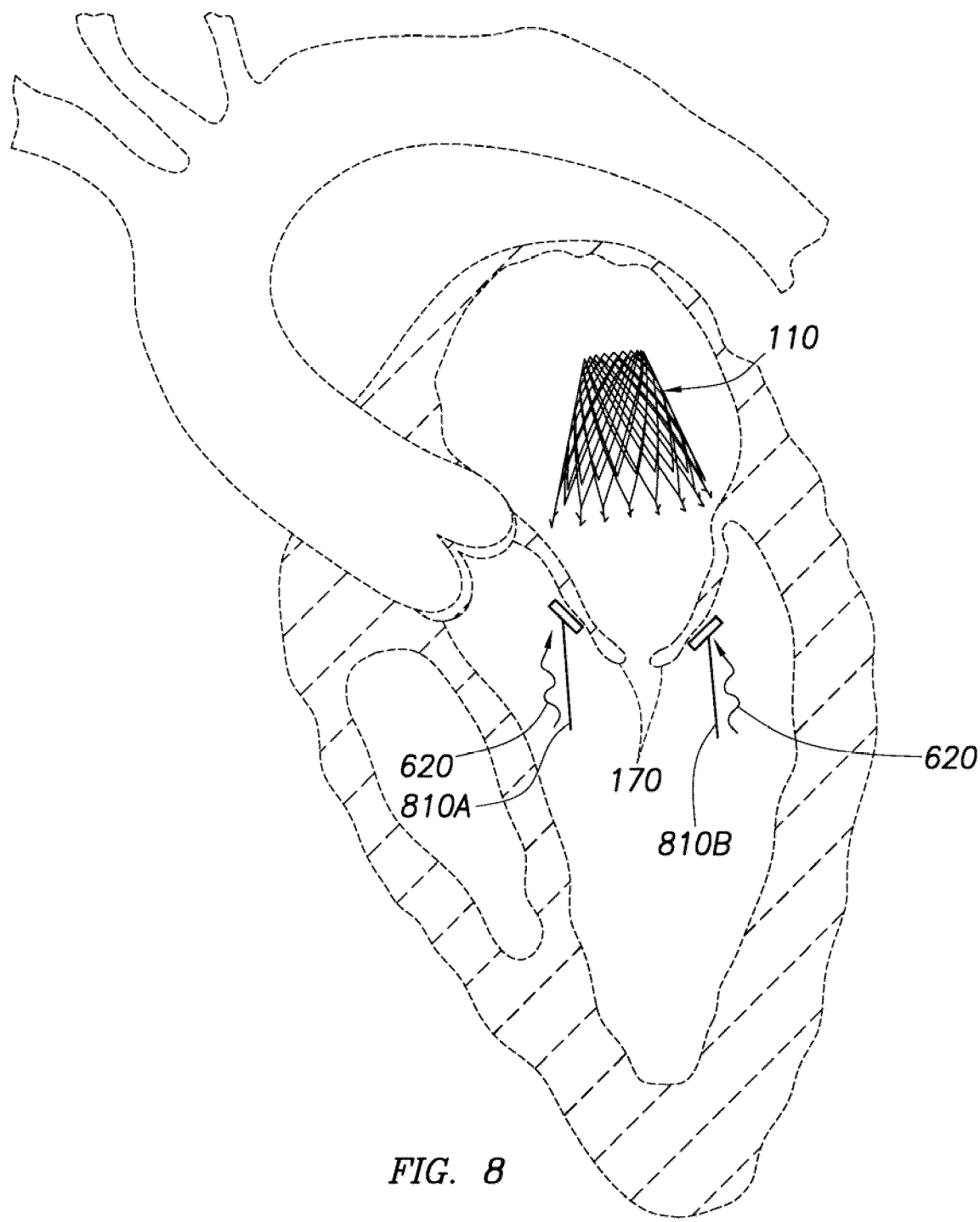
FIG. 8 illustrates an additional example embodiment of the present disclosure utilizing vibrations, in accordance with the present disclosure.

As shown in FIGS. 7 and 8, to aid in the engagement of the penetrating members 115, additional energy may be added to vibrate the tissue surrounding or below mitral valve 170. For example, as shown in FIG. 7, vibration pads 710A and 710B may deliver vibration 620 to the surrounding tissue near the barbs or hooks of penetrating members 115. Pads 710A and 710B may be used to vibrate the tissue near the barb insertion site. Pads 710A and 710B may be completely separate from implant 110 or may be connected to the same delivery system. A separate control for linear and radial motion of pads 710A and 710B may be provided to control the location to provide precise delivery of vibration 620.

As shown in FIG. 8, vibration pads 810A and 810B may also be located below mitral valve 170. This may still provide vibration 620 to facilitate the engagement of barbs or hooks of penetrating members 115 with tissue proximate mitral valve 170. As with the embodiment of FIG. 7, vibration pads 810A and 810B may be completely separate from implant 110 or may be connected to the same delivery system. A separate control for linear and radial motion of pads 810A and 810B may be provided to control the location to provide precise delivery of vibration 620.

Radio frequency (RF) is a rate of oscillation in the range of about three kHz to three hundred GHz, which corresponds to the frequency of radio waves, and the alternating currents, which carry radio signals. RF usually refers to electrical rather than mechanical oscillations. Below is a chart of common nomenclature for different frequency ranges. The range utilized for barb penetration may be somewhere between ELF and HF as the goal is small vibration and not heating of the tissue. Possible user range selection would allow for different tissue types and densities.

TABLE 1

| Frequency | Wavelength | Designation | Abbreviation |
|---|---|---|---|
| 3-30 Hz | $10^5$-$10^4$ km | Extremely low frequency | ELF |
| 30-300 Hz | $10^4$-$10^3$ km | Super low frequency | SLF |
| 300-3000 Hz | $10^3$-100 km | Ultra low frequency | ULF |
| 3-30 kHz | 100-10 km | Very low frequency | VLF |
| 30-300 kHz | 10-1 km | Low frequency | LF |
| 300 kHz-3 MHz | 1 km-100 m | Medium frequency | MF |
| 3-30 MHz | 100-10 m | High frequency | HF |
| 30-300 MHz | 10-1 m | Very high frequency | VHF |
| 300 MHz-3 GHz | 1 m-10 cm | Ultra high frequency | UHF |
| 3-30 GHz | 10-1 cm | Super high frequency | SHF |

TABLE 1-continued

| Frequency | Wavelength | Designation | Abbreviation |
|---|---|---|---|
| 30-300 GHz | 1 cm-1 mm | Extremely high frequency | EHF |
| 300 GHz-3000 GHz | 1 mm-0.1 mm | Tremendously high frequency | THF |

Vibration to enhance tissue penetration by the anchor may be delivered from a vibration source to tissue adjacent the penetration site, such as by the vibration pads discussed above. The vibration source may be embedded in the pad or other vibration interface at the distal end of an elongate control element such as a wire or tube. Alternatively, the vibration source may be located in a proximal manifold and propagate vibrational energy distally through an elongate wire or tube extending through the catheter body. The vibration source can alternatively be coupled in vibration propagating communication with either the implant frame or with each individual anchor directly, such as through the anchor driver, depending upon desired performance.

Figure 9A:
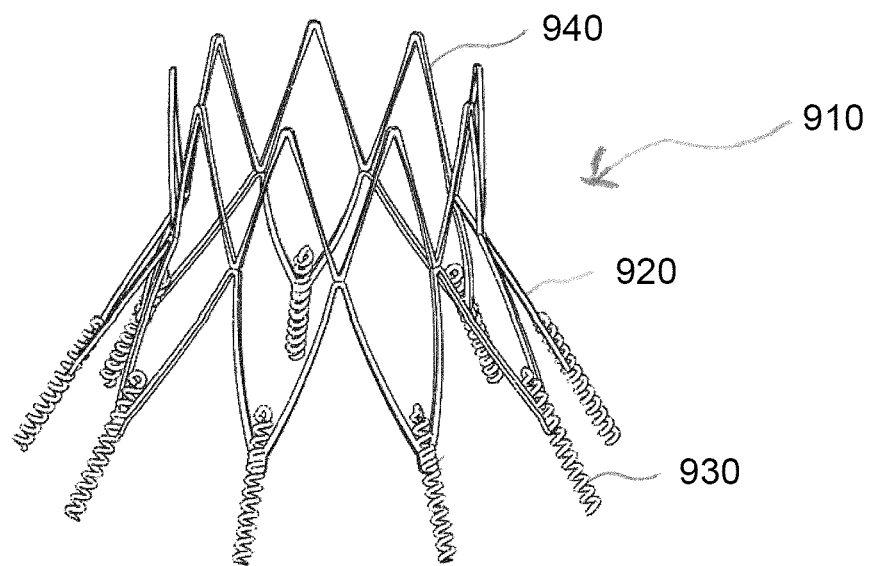
FIGS. 9A-9B are perspective views of other embodiments of implants having rotatable helical anchors for securing the implants to a valve annulus.

FIG. 9A depicts another embodiment of an implant 910. The implant 910 may have the same or similar features and/or functionalities as other implants described herein, and vice versa, except as otherwise described. Implant 910 comprises a frame 920, piercing members or anchors 930, and may include an expandable member 940. The frame 920 has a free or unconstrained state or, otherwise stated, nominal configuration as shown in FIG. 9A. The frame 920 may be made of a nickel titanium alloy, i.e. nitinol, or other shape memory alloy or metal. The frame 920 may be a dissimilar material as that of the expandable member 940. The frame 920 may be tubular with a wall circumferentially defining a central axis. The frame 920 may include angled segments as shown, and/or other segments, configurations, etc. The frame 920 as shown may be sinusoidally shaped, although its architecture could be of a diamond lattice or hexagonal lattice, for example. The frame 920 or portions thereof may incline radially outward with respect to the axis and/or with respect to the expandable member 940. The frame 920 may pivot about pivot joints located at or near interfaces with the expandable member 940. In some embodiments, fixed attachments are located at one or more of the joints between the frame 920 and the expandable member 940, for example at the interfaces of abutting apices of the frame 920 and the expandable member 940.

Anchors 930 may be metallic helical members. The anchors 930 may threadingly engage with the lower, i.e. distal, apices of frame 920. The anchors 930 may wind through a series of holes through holes drilled in the distal ends or distal apices of frame 920 (more clearly indicated by reference numerals 1050 in FIGS. 10, 11 and 12). The frame 920 may include a series of distal apices formed by the frame 920 proximate the distal diameter. A series of holes in each of the distal apices may be sized and spaced to receive therethrough a corresponding helical anchor 930 for rotational engagement of the distal apex by the corresponding helical anchor 930. The holes may be the same or similar to holes 1050 described for example with respect to FIG. 10. The anchors 930 may be advanced distally, and in some embodiments retracted proximally, in a rotational or corkscrew type manner. The anchors 930 may extend distally relative to the frame 920. For example, as the anchors 930 are rotated, the anchors 930 may move in the distal direction while the frame 920 is stationary. In some embodiments, the frame 920 may move distally while the anchors 930 move farther distally relative to the frame 920. Thus, the frame 920 may be located in the preferred position and the anchors 930 may then be moved distally to secure into heart tissue while the frame 920 remains axially stationary or approximately axially stationary. This allows for better accuracy with positioning of the implant 910 because there is less movement of the frame 920 while the anchors 930 are being secured to heart tissue. Further, the anchors 930 engage the frame 920, as described, for example through the series of holes in distal apices of the frame 920. This allows for a secure attachment between the anchors 930 and the frame 920 without the need for additional structure or features. The arrangement of the holes and the corresponding receiving of the anchor 930 therethrough in each apex allows for an axially secure engagement of the anchor 930 and the frame 920 while still allowing for movement of the anchor 930 by driving it with the driver 952. By axially secure it is meant that the anchor 930 will not move axially relative to the frame 920 in the absence of sufficient rotational force acting on the anchor 930, such that the anchor 930 and frame 920 are rotationally secured together after removal of the rotational force from the driver 952 thereby impeding further axial movement of the anchor 930 relative to the frame 920. The configuration of the series of holes in the frame 920 and the helical shape of the anchors 930 allows for such advantages. In FIG. 9A, the anchors 930 are shown extended distally, for example in the final stage of deployment into cardiac tissue proximate the mitral annulus. The mitral annulus is that region of transition from the left atrium to the left ventricle and proximate and above the area where the leaflets of mitral valve 170 (see FIG. 5) hinge from the left ventricle.

The implant 910 may include the expandable portion or member 940. The expandable member 940 may be stent-like. The expandable member 940 may be tubular with a wall circumferentially defining a central axis. The expandable member 940 may include angled segments as shown, and/or other segments, configurations, etc. While shown in the shape of a sinusoid, the expandable member 940 may otherwise have a diamond lattice or hexagonal lattice architecture, for example. The expandable member 940 may be a dissimilar material as that of the frame 920. The expandable member 940 may be made of metallic alloys such as stainless steel, cobalt chromium, platinum iridium and the like. The expandable member 940 may be collapsed or crimped for insertion into a delivery system and forcibly expanded, so as to undergo plastic deformation, to invert the frame 920. As shown in FIG. 9A, expandable member 940 may be integral with frame 920, for example a unified, monolithic portion or region of the frame 920. In some embodiments, the expandable member 940 is fixedly attached to frame 920 by bonding, welding, sutures, metallic bands crimped on to each structure, or otherwise connected in a fixed relationship to frame 920. In some embodiments, the expandable member 940 can have other coupling interactions with the frame 920, such as a friction fit, expansive force keeping the frame 920 secured with the expandable member 940, etc.

Implant 910 is loaded into the distal end of a delivery system (not shown), by compressing or collapsing the frame 920. Anchors 930 would be initially retracted for loading and delivery. Once positioned in a desired location proximate the mitral valve annulus, frame 920 is advanced out of the delivery system and its distal apices are abutted to the target heart tissue for anchor placement. The helical anchors are then advance, by rotation thereof, into the target cardiac tissue thereby anchoring implant 910 into the region of the mitral valve annulus. Implant 910 is then fully released from the delivery system.

After implant 910 is fully released from the delivery system, expandable member 940 is then forcibly expanded, such as by a dilatation balloon, causing frame 920 to invert. Inversion of frame 920 causes the anchor bearing distal end of frame 920 to taper or contract, causing the mitral valve annulus to reduce in size thus limiting the mitral valve regurgitation.

Figure 9B:
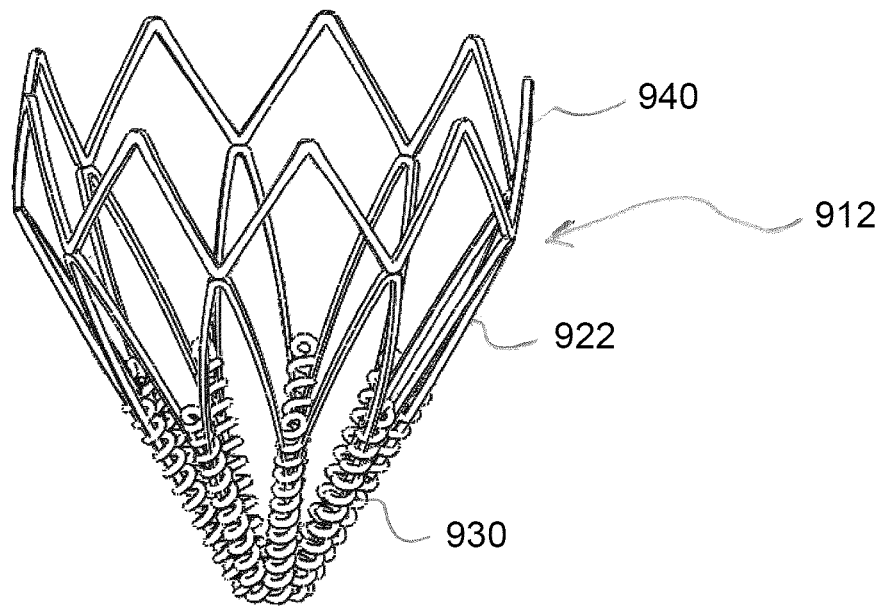

FIG. 9B is another embodiment of an implant 912. The implant 912 may have the same or similar features and/or functionalities as the implant 910, and vice versa, except as otherwise noted. The implant 912 comprises the expandable member 940 and piercing members or anchors 930. A frame 922 extends circumferentially about a central longitudinal axis. The frame 922 is formed to have as its free or unconstrained configuration somewhat opposite to that of the frame 920 of the implant 910. For example, as shown the lower, distal end as oriented, the end engaging anchors 930, may be smaller in diameter than the opposite upper, proximal end of the frame 922. The frame 922 may therefore incline radially inward relative to the central axis and/or relative to the expandable member 940. The frame 922 and the expandable member 940 may be formed of dissimilar materials. The frame 922 may be formed of similar materials as the frame 920 described with respect to FIG. 9A.

To perform the procedure of influencing the size of the mitral annulus, for example for treating the patient's mitral regurgitation, the expandable member 940 and the larger, proximal end of frame 922 are compressed or crimped and loaded into the distal end of a delivery system (not shown). This action also causes the distal or narrower end of frame 930 to invert. Such inversion must be restrained for loading into the delivery system.

Once positioned in the desired location proximate the heart valve annulus, such as the mitral valve annulus, the frame 922 is advanced out from the distal end of the delivery system, inverting as it is no longer constrained by the delivery system and expandable member 940 remains in the crimped configuration. The distal ends or distal apices of frame 922 are then positioned in abutting relationship to the target cardiac tissue proximate the mitral valve annulus. Helical piercing members 930 are then rotationally advanced into and in engagement with the target heart tissue in a manner very similar to the helical screw of a corkscrew advancing through a cork. The expandable member 940 is then expelled from the delivery system and forcibly expanded, for example by dilatation balloon which balloon could be an integral component of the delivery system. Expansion of the stent-like expandable member 940 causes frame 922 to revert to its nominal or free state thereby causing its distal apices and helical anchors to become narrower in diameter reducing the size of the mitral annulus and limiting the degree or extent of mitral regurgitation.

Figure 10:
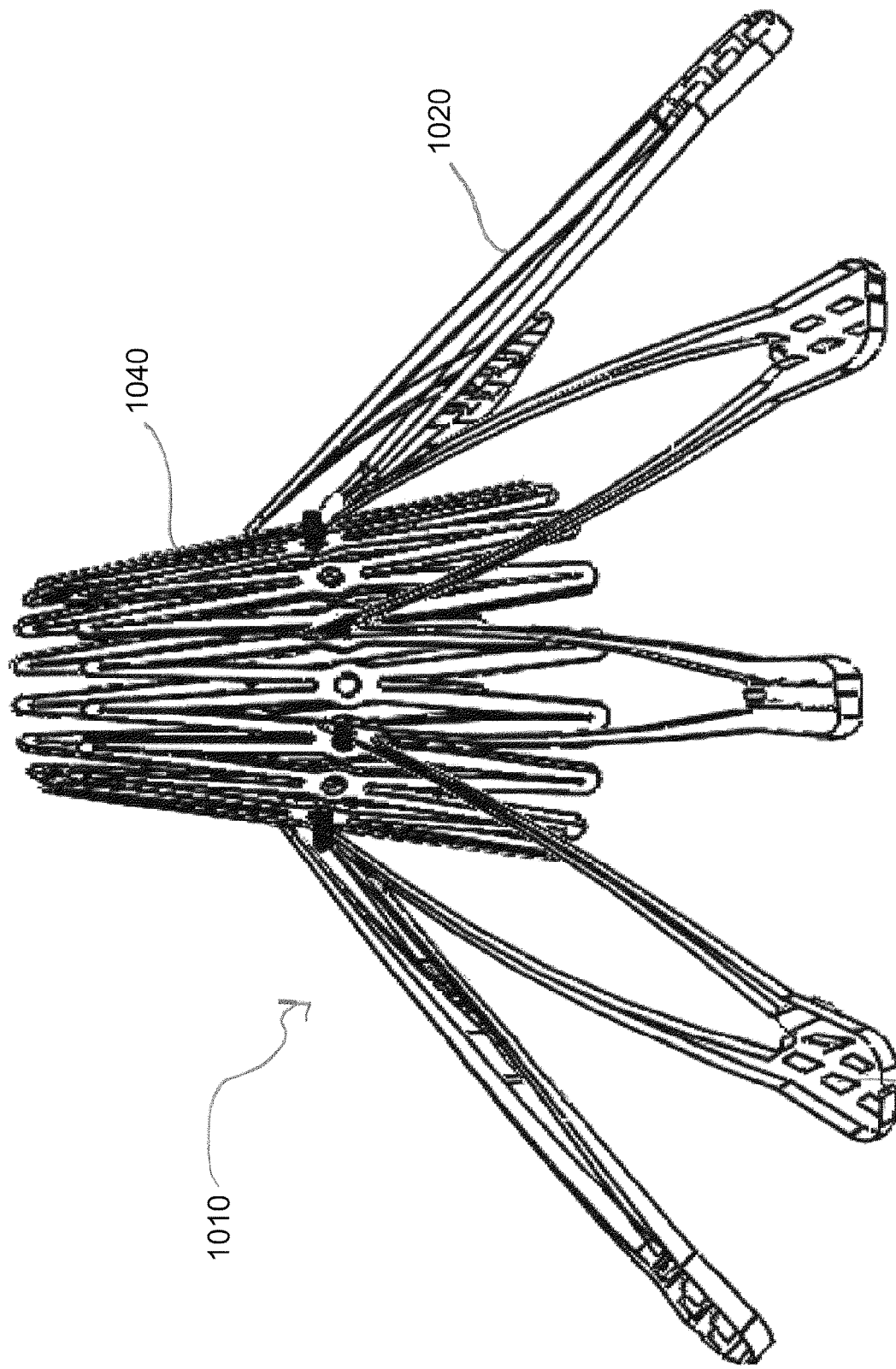
FIG. 10-12 are perspective views of another embodiment of an implant, having an expandable tubular element, and configured to be secured to a valve annulus with helical anchors.
Figure 11:
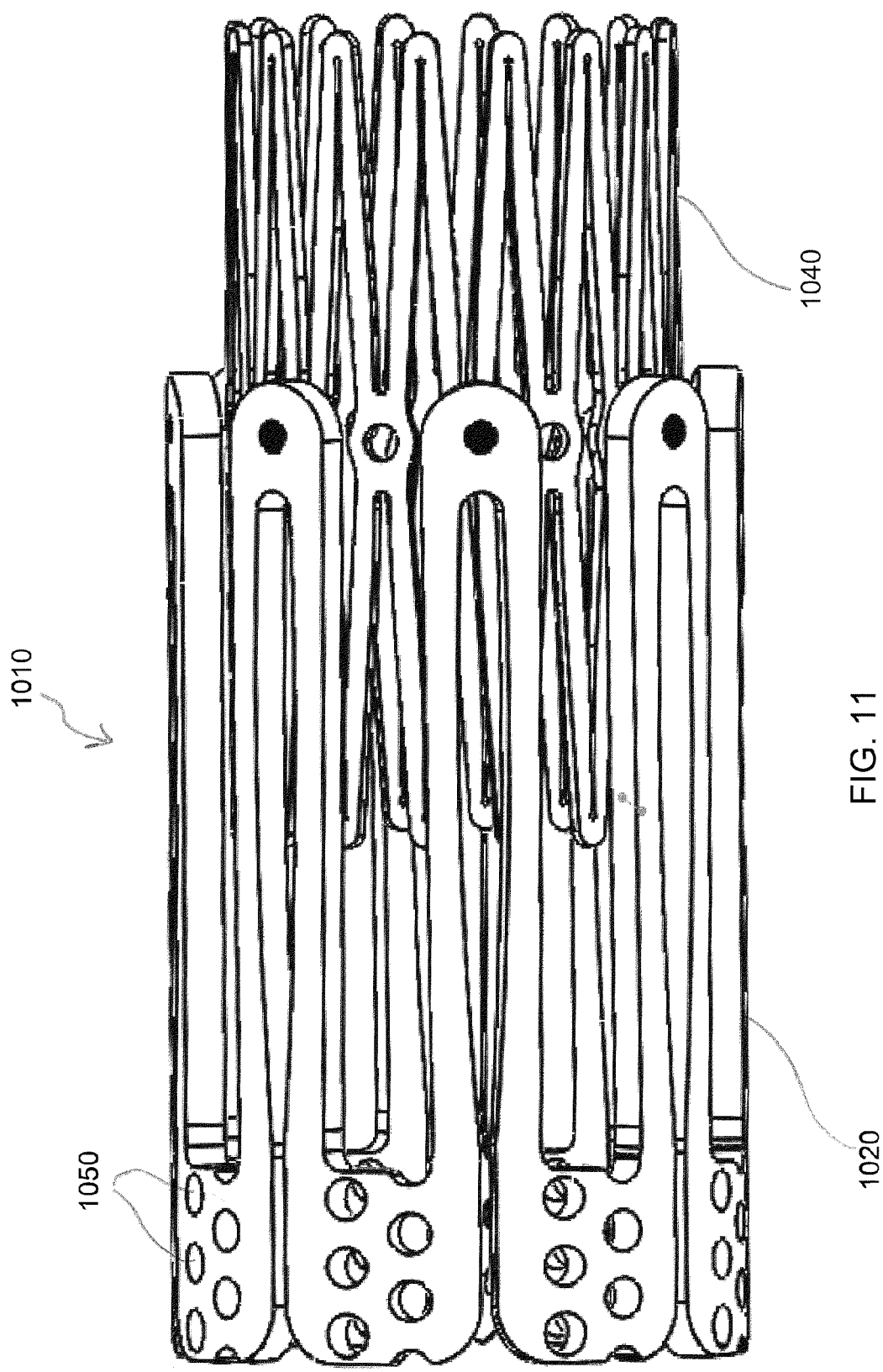
Figure 12:
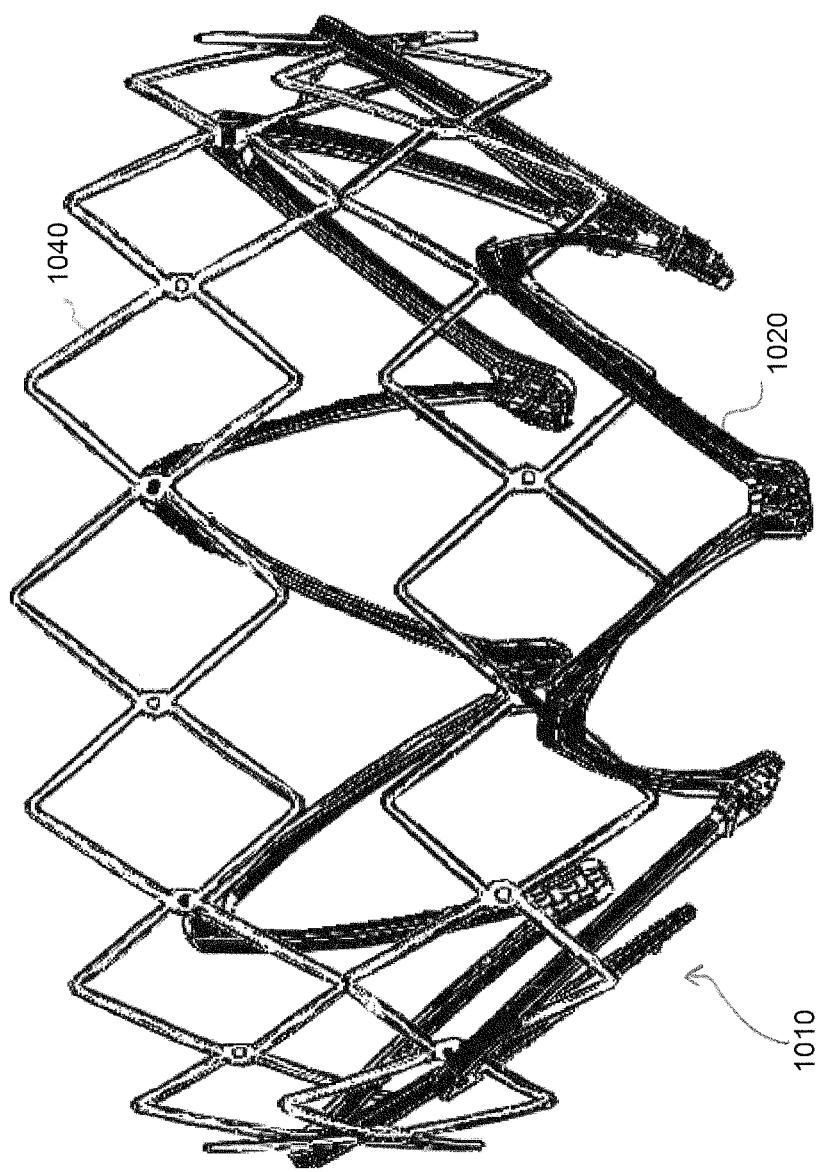

FIGS. 10, 11 and 12 are various views of another embodiment of an implant 1010. In this embodiment, the implant 1010 has a frame 1020 and an expandable member 1040 that are not formed as an integral implant, as for example in FIGS. 9A and 9B. Rather expandable member 1040 is positioned within frame 1020 proximate the proximal end thereof. Frame 1020 is made from a nickel titanium alloy, such as Nitinol, whereas expandable member 1040 is preferably made of metallic alloys such as stainless steel, cobalt chromium, platinum iridium and the like.

FIG. 10 shows frame 1020 in its free or unconstrained state with expandable member 1040 crimped and positioned within frame 1020. One or more holes 1050 are pre-drilled in the distal ends or apices of frame 1020 and oriented to accommodate the pitch of helical anchors (not shown for clarity) such as the anchors 930 of FIGS. 9A and 9B. The anchors 930 may be rotated through the holes 1050 to advance the anchors 930 distally, i.e. downward as oriented in the figure. In some embodiments, the anchors 930 may be rotated in the opposite direction through the holes 1050 to retract the anchors 930 in the opposite, proximal direction. FIG. 11 shows the frame 1020 in a constrained configuration and implant 1010 ready for loading into the distal end of a delivery system (not shown). FIG. 12 shows implant 1010 in what would be its deployed configuration. While expandable member 1040 is shown to have a diamond like lattice configuration, it is contemplated that it may also take the form of a sinusoid or a hexagonal configuration.

Delivery of implant 1010 may be conducted in similar respect to the embodiment of FIG. 9A. More specifically, implant 1010 is loaded into the distal end of a delivery system (not shown), by compressing or collapsing frame 1020 as shown in FIG. 11. Once positioned in a desired location proximate the mitral valve annulus, frame 1020 is advanced out of the delivery system and its distal apices are abutted to the target heart tissue for anchor placement. The helical anchors (not shown) are then advance, by rotation thereof, into the target cardiac tissue thereby anchoring implant 1010 into the region of the mitral valve annulus. Implant 1010 is then fully released from the delivery system.

After implant 1010 is fully released from the delivery system, expandable member 1040 is then forcibly expanded, such as by a dilatation balloon, causing frame 1020 to invert as shown in FIG. 12. Inversion of frame 1020 causes the anchor bearing distal end of frame 1020 to taper or contract, causing the mitral valve annulus to reduce in size thus limiting the mitral valve regurgitation.

Figure 13:
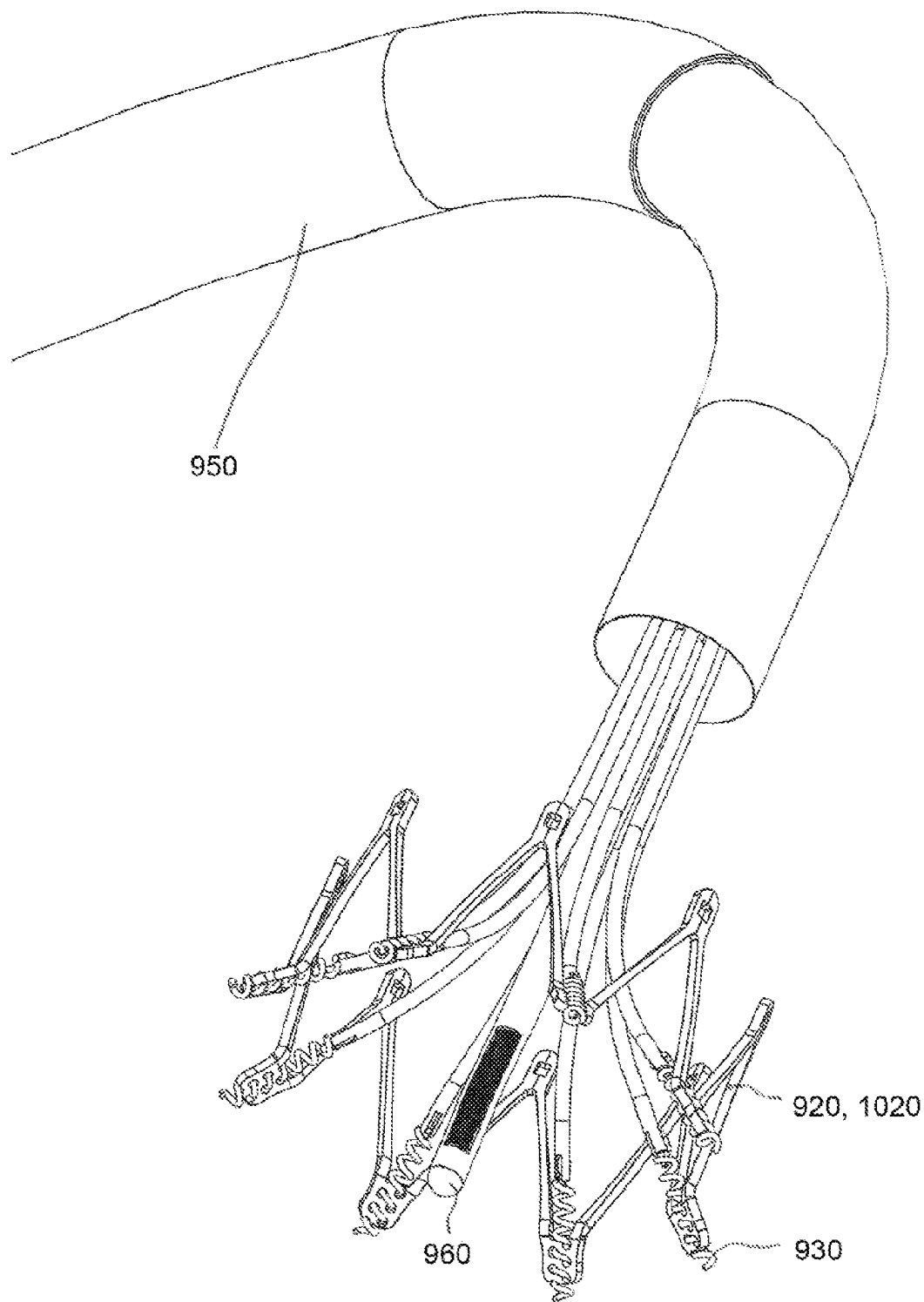
FIG. 13 is a perspective view of an embodiment of a delivery system shown delivering an embodiment of the implant of FIGS. 10-12.

FIG. 13 shows an exemplary steerable delivery system 950, including for example a catheter or catheter lumen, suitable for delivery of the various implant embodiments described herein. FIG. 13 depicts an embodiment of the implant 1010 of FIGS. 10-12, but it is understood that the delivery system 950 can be used to delivery other implants, including but not limited to the implant 912 of FIG. 9B and the implant 910 of FIG. 9A, the latter of which is further shown in and described with respect to FIG. 14. For example, a similar delivery system 950 may be used for the implant 912 embodied in FIG. 9B. For brevity and since the expandable members are different between the aforementioned embodiments, the expandable members 1040 are not shown in FIG. 13.

The delivery system 950 may include a tube or tube-like structure having one or more lumens extending therethrough. For instance, the delivery system 950 may include an elongated tube or delivery catheter having one or more openings, i.e. lumens, extending therethrough and configured to receive therein, or having therein, corresponding features of the delivery system 950, including but not limited to the guide wire 160, the catheter 140, one or more of the drivers 952, and the intracardiac echo catheter 960. In some embodiments, the delivery system 950 includes a delivery catheter having a lumen to guide the delivery catheter over the guide wire, another lumen or lumens that include(s) the rotatable drivers 952, the implant 912 in a constrained delivery configuration located at a distal end of the delivery catheter, and a sheath covering the distal end of the catheter. Delivery system 950 is advanced transfemorally, either through the femoral vein and transeptally to the left atrium or through the femoral artery up through the aortic arch and then passed the aortic and mitral valves into the left atrium. Once positioned above mitral annulus and proximate the target heart tissue, the implant is partially released, releasing the frame portion 920, 1020. Frame 920, 1020 is now unconstrained and able to return to its nominal or free state as shown in FIG. 13.

Helical piercing members 930 are then rotationally advanced into the target cardiac tissue, anchoring the implant to the interior heart wall above the mitral annulus. The implant and expandable member 940, 1040 is then released from delivery system 950. At such time, the stent like member 940, 1040 is forcibly expanded causing the frame 920, 1020 to invert. The distal end of apices and helical anchors 930 are then cinched inwardly reducing the diameter of the distal end of frame 920, 1020 causing a corresponding reduction in the size of the mitral annulus. This reduction in size of the mitral annulus, allows the mitral valve leaflets to better, if not completely, coapt reducing the severity of the patient's mitral regurgitation.

In a further embodiment of the present invention, an intracardiac echo catheter 960 is incorporated in delivery system 950. Catheter 960 could be included in a lumen of delivery system 950, either internally as shown, or alongside implant delivery system 950. By rotating catheter 960 within the left atrium and proximate the mitral valve annulus, the relative position of the implant with respect to the mitral valve leaflets can be determined. This allows for accurate positioning of helical anchors 930 into the target heart tissue proximate the mitral annulus without piercing the mitral valve leaflets.

Figure 14:
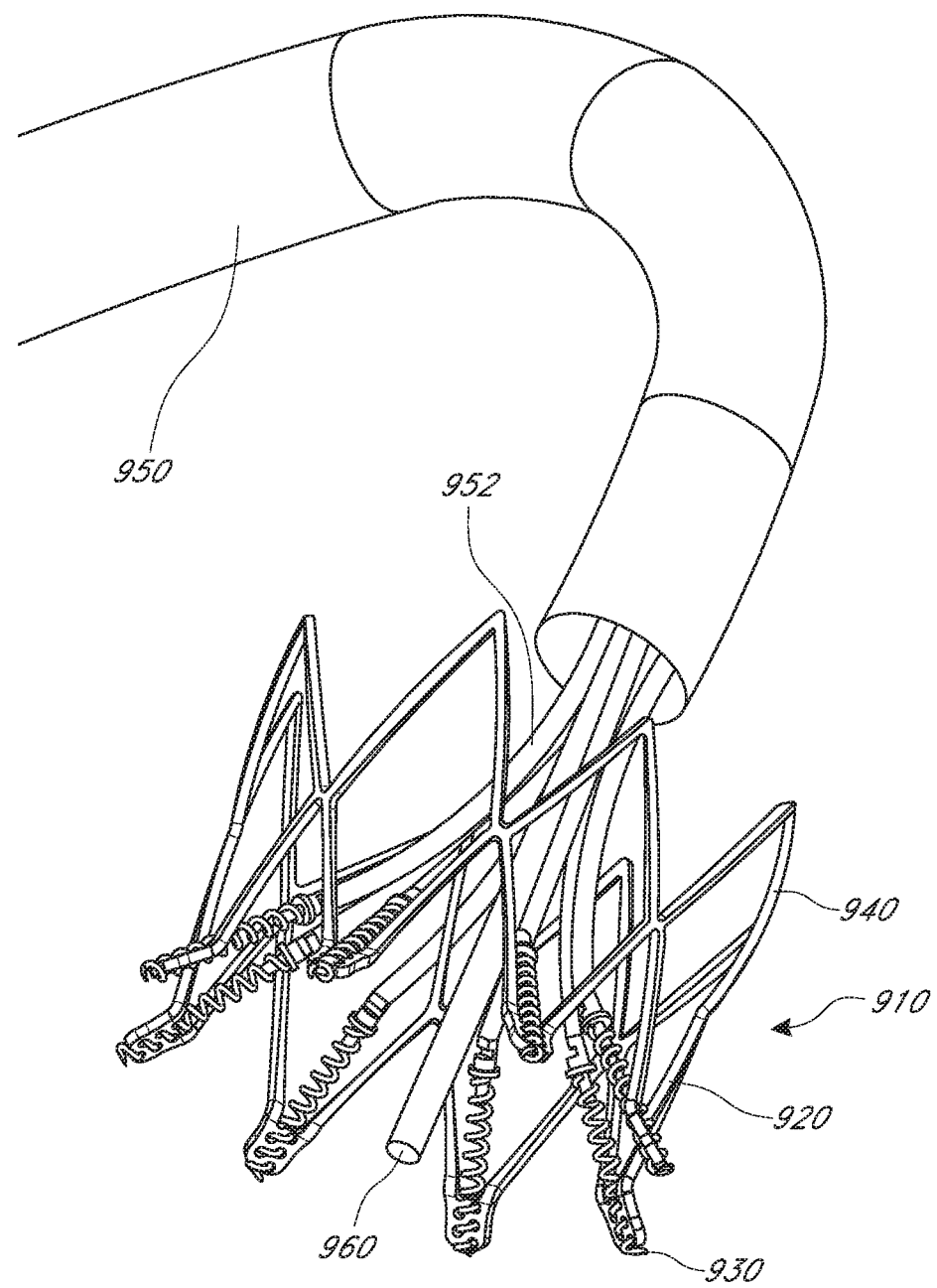
FIG. 14 is a perspective view of an embodiment of a delivery system shown delivering the implant of FIG. 9A.

FIG. 14 depicts the steerable delivery system 950 being used to deliver the implant 910 of FIG. 9A. The description of the delivery system 950 above with respect to FIG. 13 applies to use of the system 950 with the implant 910, and vice versa, except as otherwise noted. As shown in FIG. 14, the implant 910 thus includes the frame 920 and expandable member 940, shown as integral with the frame 920. In some embodiments, the implant 910 may only include the frame 920. The delivery system 950 may or may not include the intracardiac echo catheter 960, as described above.

As shown in FIG. 14, a plurality of rotational drivers 952 extends out through a distal opening of a lumen of the delivery catheter and/or sheath of the delivery system 950. Each driver 952 may extend through a corresponding lumen of the delivery system 950. In some embodiments, more than one or all of the drivers 952 may extend through the same lumen of the delivery system 950. A guide wire, such as the guide wire 160, may also be incorporated into the delivery system 950, and may extend through a lumen of the delivery system 950.

The drivers 952, only some of which are labelled for clarity, are each engaged with a corresponding rotational anchor 930. The drivers 952 may be pre-engaged with the anchors 930 within the delivery catheter of the delivery system 950 before insertion of the distal end of the delivery system 950 into the atrium. The drivers 962 may be mechanically engaged with the anchors 930 in a variety of suitable approaches. For example, the drivers 962 may have a clevis type fitting as shown configured to surround the proximal end of the anchors 930. The drivers 952 may extend over, on, under, etc. the proximal ends of the anchors 930 and then be rotated to transmit rotation to the anchors 930. In some embodiments, the anchors 930 may have recesses or other tool-receiving portions engaged by the drivers 952 such that rotation of the drivers 952 is transmitted to the anchors 930. In some embodiments, the drivers 952 may include socket type fittings that surround the anchors 930. In some embodiments, the anchors 930 may have internally-threaded blind holes through which corresponding externally-threaded members of the drivers 952 are received. These are merely some examples of how the drivers 952 may be engaged with the anchors 930, and other suitable approaches may be implemented. With the implant 910 in position for anchoring to the annulus, a proximal end of the drivers 962 may be manipulated by the user, for example rotated by the surgeon, to rotate the anchors 930 and thereby advance the anchors 930 into heart tissue, as described herein, to secure the implant 910 with the heart tissue. Each driver 952 may be actuated simultaneously, some may be actuated simultaneously, or they may be actuated sequentially. The anchors 930 may extend distally relative to the frame, as described herein.

FIGS. 15A-15D show sequential views of an embodiment of a transcatheter delivery system for delivering the implant 910 showing an embodiment of a method for the delivery, positioning and anchoring of the implant 910 for resizing the native valve annulus. The various delivery systems as described herein may be used. As shown, the delivery system may include the sheath 150, the catheter 140 and the guide wire 160. The sheath 150, the catheter 140, the guide wire 160 and the implant 910 are configured for transcatheter delivery of the implant 910 to the heart. The implant 910 may be delivered by the delivery system percutaneously by catheter through an opening in the femoral vein. The implant 910 may be advanced through the femoral vein into the vena cava and into the right atrium. The distal ends of the sheath 150, catheter 140, and guide wire 160 are configured to extend through the opening in the femoral vein, through the femoral vein and into the right atrium of the heart, and through the septum of the heart into the left atrium.

Figure 15A:
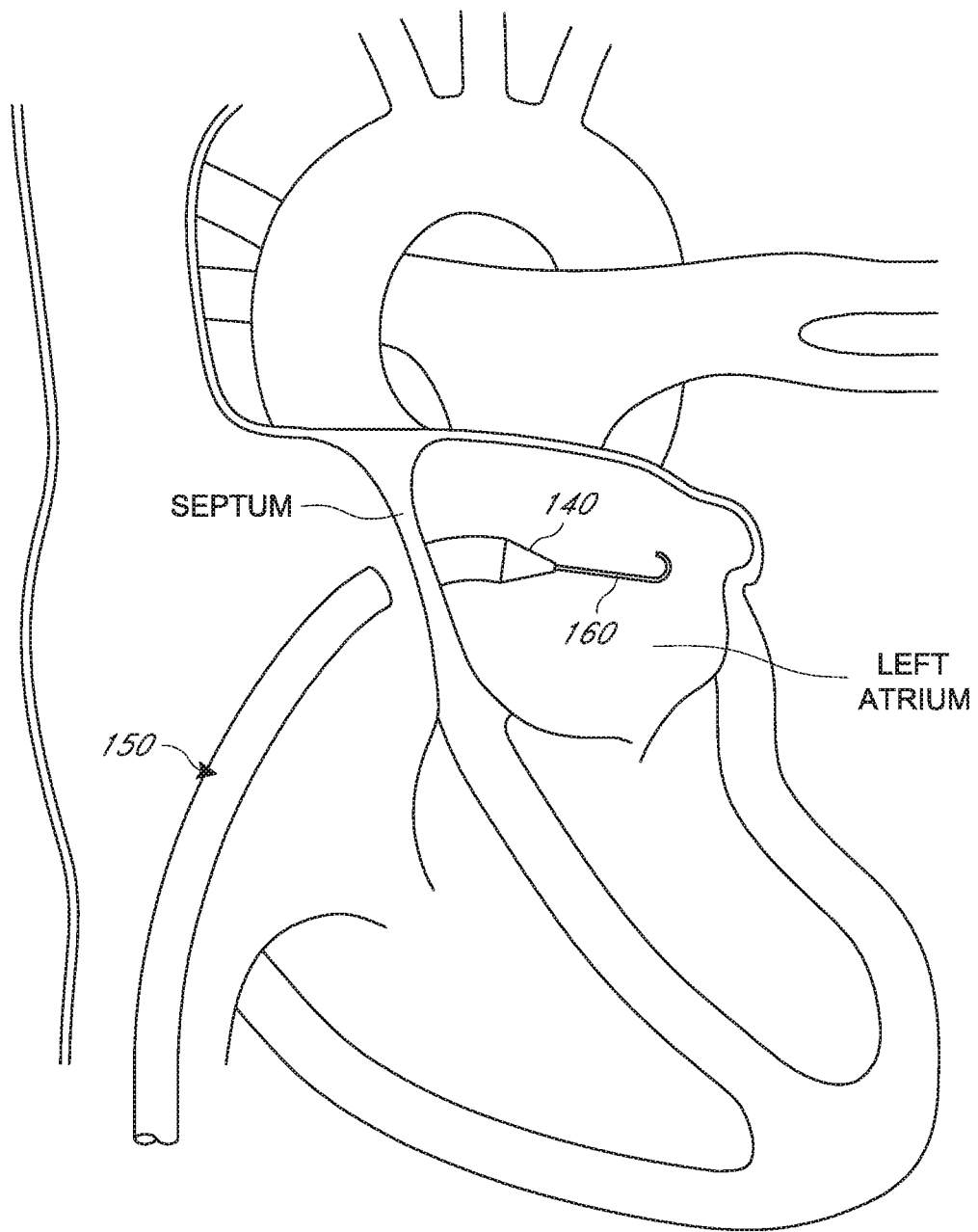
FIGS. 15A-15D are sequential views of an embodiment of a transcatheter delivery system for delivering the implant of FIG. 9A showing an embodiment of a method for the delivery, positioning and anchoring of the implant.
Figure 15B:
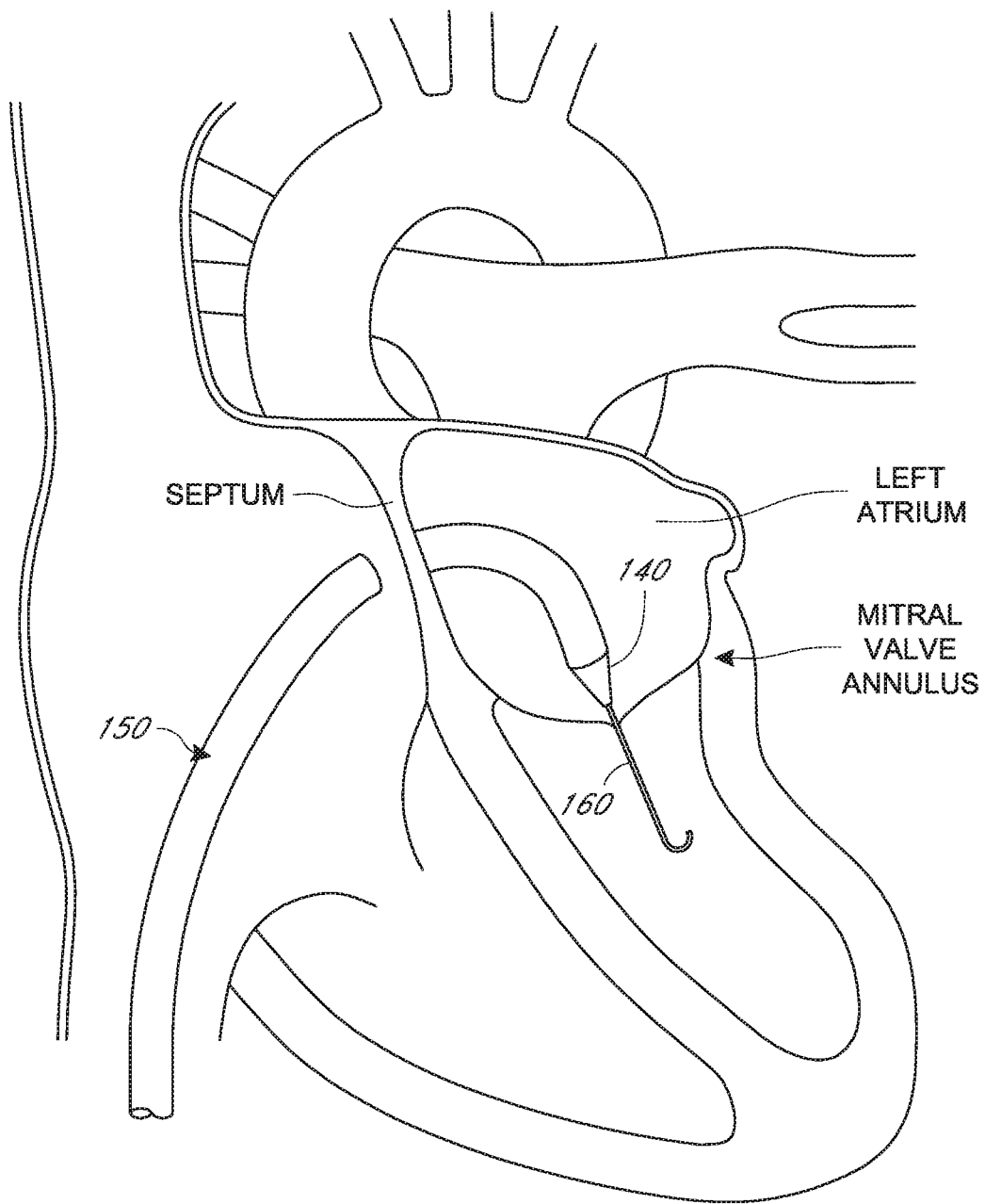
Figure 15C:
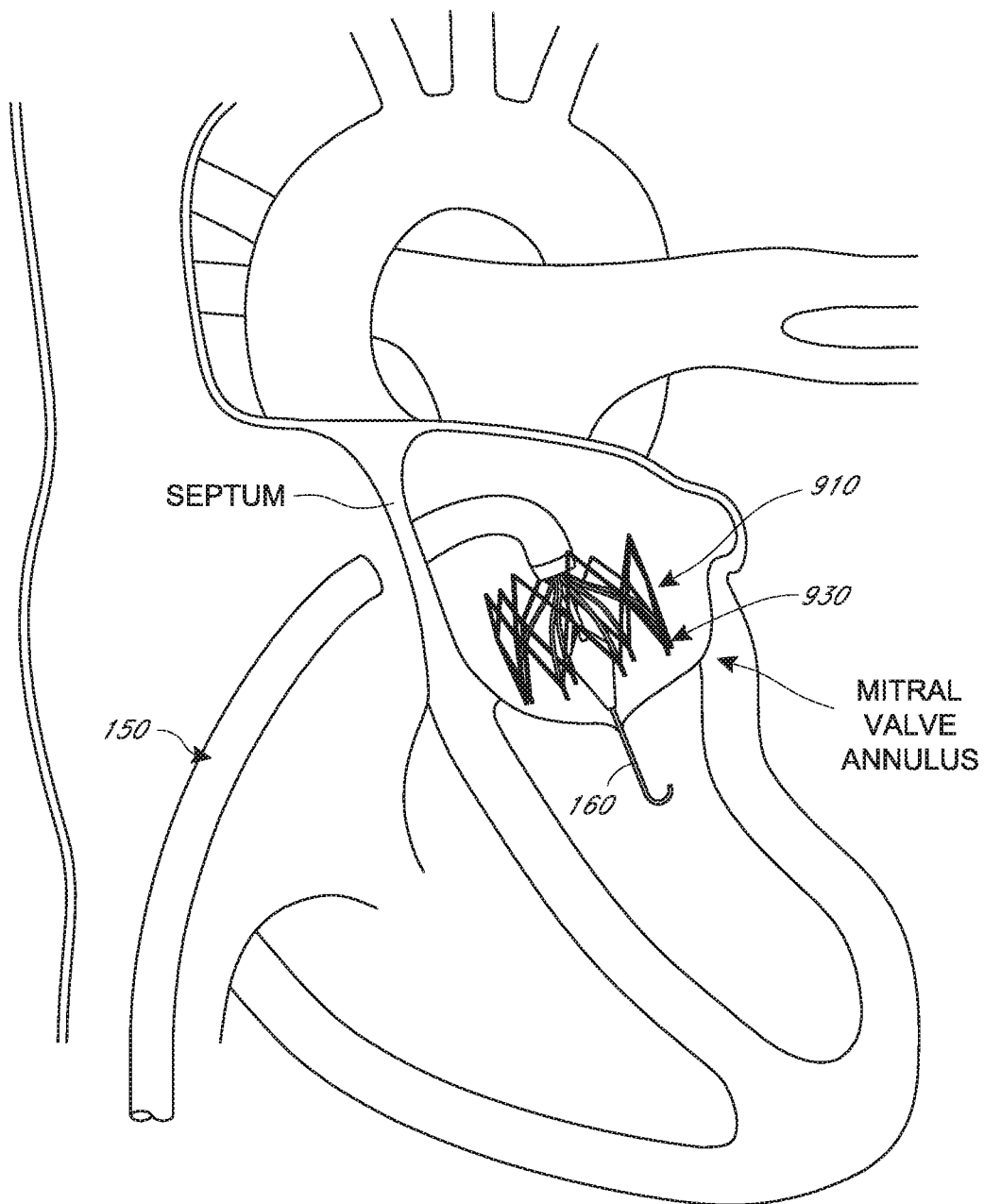
Figure 15D:
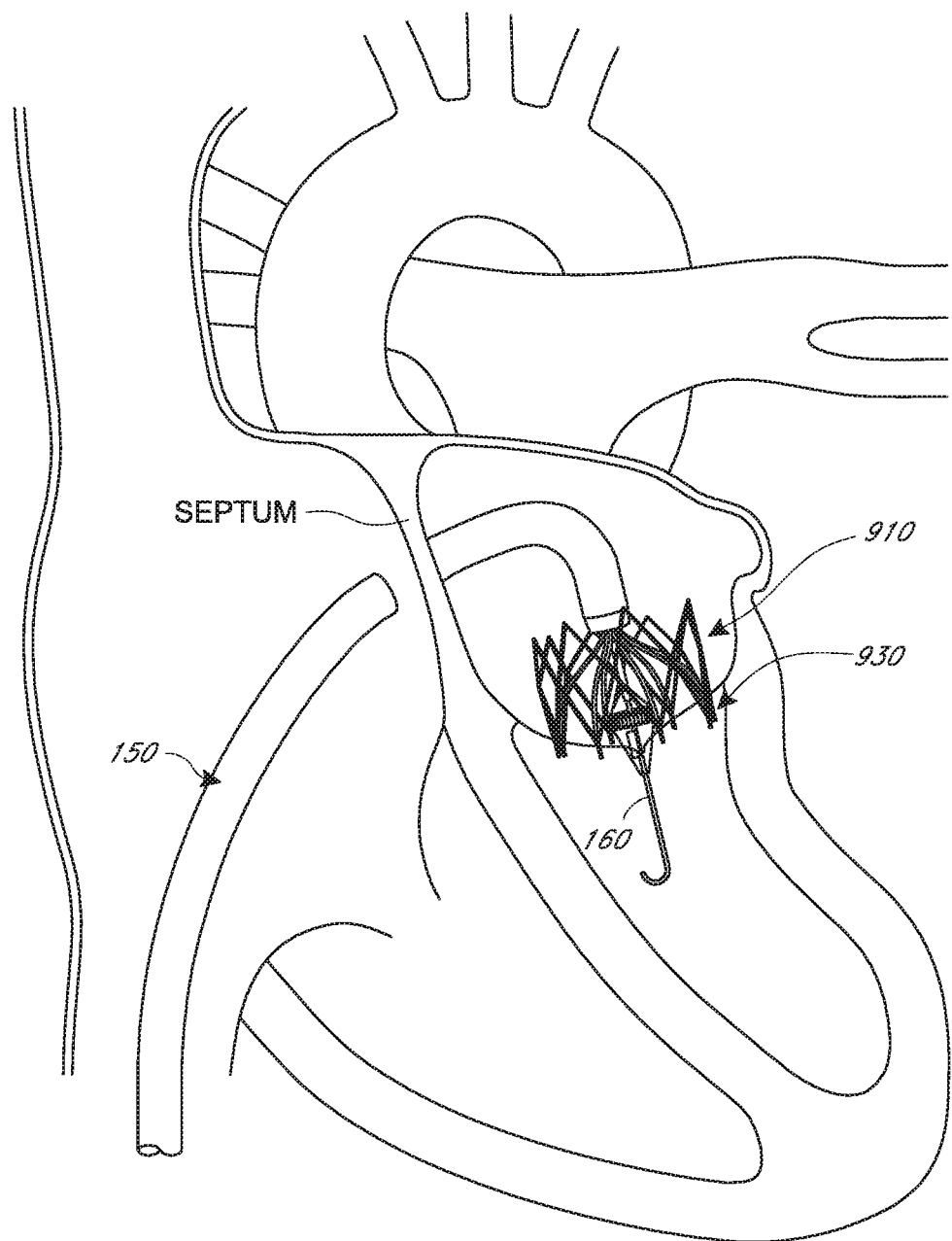

As shown in FIG. 15A, the guidewire 160 may be advanced through the septum separating the upper chambers of the heart and the sheath 150 and catheter 140 may be advanced to that position along the guide wire 140. The distal end of the catheter 140 is advanced to a position above the heart valve annulus, for example, the mitral valve annulus, as shown in FIG. 15B. FIG. 15C shows the implant 910 expelled from the distal end of the sheath 150 above and proximate to the mitral valve annulus. In some embodiments, a series of images may be taken, for example with an intracardiac echo catheter, to properly position the anchors 930 for insertion into the mitral valve annulus tissue. As shown in FIGS. 15C and 15D, the anchors 930 may be rotationally engaged by rotational drivers of the delivery system, such as the drivers 952 described herein, for rotation and distal advancement of the anchors 930 into the heart valve annulus. In some embodiments, a circumferential image may be captured to confirm that all anchors 930 are appropriately placed and anchored in the mitral valve annulus tissue above the mitral valve leaflets. If one or more anchors 930 are not positioned or anchored properly, the drivers 952 may reverse the direction of rotation to rotationally retract the anchors in the proximal direction. The anchors 930 can then be repositioned and re-anchored prior to removal of the drivers 952.

Though a particular path of transcatheter delivery is described with respect to FIGS. 15A-15D, a variety of other delivery paths and approaches may be employed, including but not limited to the paths shown and described with respect to FIGS. 1A-1F, trans-apical delivery, etc. In addition, any of the features and/or functionalities of the delivery system and associated methods described with respect to FIGS. 1A-1F may be incorporated with respect to the delivery system and methods described with respect to FIGS. 15A-15D, and vice versa. Therefore, for example, with regard to the delivery system and methods described with respect to FIGS. 15A-15D, the implant 910 may "invert" as described herein, an expandable or fixed ring 320 may be utilized as described, the location ring 120 may be inserted below the valve, etc.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. For example, various embodiments may perform all, some, or none of the steps described above. Various embodiments may also perform the functions described in various orders.

Although the present disclosure has been described above in connection with several embodiments; changes, substitutions, variations, alterations, transformations, and modifications may be suggested to one skilled in the art, and it is intended that the present disclosure encompass such changes, substitutions, variations, alterations, transformations, and modifications as fall within the spirit and scope of the appended claims.

What is claimed is:

1. A delivery system and implant for delivering the implant within the heart for reducing the size of a heart valve annulus, the delivery system and implant comprising:
   a plurality of drivers configured to extend through one or more lumens of the delivery system; and
   the implant configured for delivery within the heart by traveling through the one or more lumens of the delivery system, the implant comprising:
   a tubular body comprising a frame comprising a plurality of struts, wherein adjacent pairs of struts are joined to form a plurality of proximal and distal apices, the tubular body defining a proximal diameter and a distal diameter, the tubular body having a first structural configuration in which the proximal diameter is smaller than the distal diameter and a second structural configuration in which the proximal diameter is larger than the distal diameter; and
   a plurality of anchors connected to the tubular body proximate the distal diameter of the frame; and
   an expandable member coupling the plurality of proximal apices of the frame, expansion or contraction of the expandable member causing inversion of the frame between the first and second structural configurations.

2. The delivery system of claim 1, wherein:
   the drivers are rotatable;
   the plurality of anchors are helical;
   a series of holes is formed in each of the distal apices, the series of holes sized and spaced to receive therethrough a corresponding helical anchor for rotational engagement of the distal apex by the corresponding helical anchor; and
   the plurality of helical anchors are configured to be rotated by the plurality of rotatable drivers to advance the plurality of helical anchors distally relative to the frame to penetrate the heart valve annulus.

3. The delivery system of claim 1, wherein the plurality of drivers and the implant are configured for transcatheter delivery of the implant to the heart.

4. The delivery system of claim 1, further comprising a delivery catheter comprising the one or more lumens of the delivery system, wherein a distal end of the delivery catheter is configured to advance through an opening in the femoral vein, through the femoral vein and into the right atrium of the heart, and through the septum of the heart into the left atrium.

5. The delivery system of claim 1, further comprising a location ring configured to be located on a side of the heart valve opposite the implant and to couple with the implant.

6. The delivery system of claim 1, further comprising a location ring separate from the implant and configured to be located on a side of the heart valve opposite the implant to assist in positioning the implant.

7. The delivery system of claim 6, wherein the location ring is configured to be removed from the heart after the implant is positioned and the plurality of anchors penetrate the heart valve annulus.

8. The delivery system of claim 1, comprising one lumen configured to receive therethrough an intracardiac echo catheter for visualizing a position of the implant relative to the mitral valve annulus.

9. The delivery system of claim 8, further comprising the intracardiac echo catheter.

10. The delivery system of claim 1, wherein the expandable member is an expandable tubular member coupling together the proximal apices at the proximal end of the frame of the tubular body of the implant and configured to expand to increase the proximal diameter of the frame.

11. The delivery system of claim 10, wherein the expandable member comprises proximal and distal apices, the distal apices of the expandable member being coupled with the proximal apices of the frame of the tubular body of the implant.

12. The delivery system of claim 1, wherein the expandable member is integral with the frame.

13. An implant for reducing the size of a heart valve annulus, the implant comprising:
a tubular body comprising a frame defining a proximal diameter and a distal diameter, the tubular body comprising a plurality of struts, wherein adjacent pairs of struts are joined to form a plurality of proximal and distal apices, the tubular body having a first structural configuration in which the proximal diameter is smaller than the distal diameter and a second structural configuration in which the proximal diameter is larger than the distal diameter;
a plurality of anchors connected to the tubular body proximate the distal diameter of the frame and configured to penetrate the heart valve annulus; and
an expandable member coupling the plurality of proximal apices of the frame, expansion or contraction of the expandable member causing inversion of the frame between the first and second structural configurations.

14. The implant of claim 13, wherein:
the expandable member is an expandable tubular member with angled segments forming proximal and distal apices, the distal apices of the expandable member being coupled with the proximal apices of the frame of the tubular body of the implant; and
when force is applied to the expandable member, the expandable member expands and engages the proximal end of the frame causing the frame to invert from the first structural configuration to the second structural configuration.

15. The implant of claim 14, wherein the expandable tubular member is integral with the proximal end of the frame.

16. The implant of claim 13, wherein the implant is configured to be contracted to a delivery configuration for transcatheter delivery of the implant to the heart by a delivery system.

17. The implant of claim 16, wherein the expandable member is an expandable tubular member coupled with a proximal end of the frame of the tubular body of the implant, wherein contracting the expandable tubular member for transcatheter delivery causes the proximal diameter of the frame to decrease relative to an unconstrained state, which causes the distal diameter of the frame to increase relative to the unconstrained state such that the proximal and distal diameters of the frame are approximately the same when delivered.

18. The implant of claim 13, wherein:
the expandable member is tubular and couples together the proximal apices of the frame of the tubular body of the implant; and
the tubular body is configured to transition from the first structural configuration to the second structural configuration by application of an expansive force to the tubular body proximate the proximal diameter via the expandable member.

19. An implant for reducing the size of a heart valve annulus, the implant comprising:
a tubular body comprising a frame defining a proximal diameter and a distal diameter, the tubular body comprising a plurality of struts, wherein adjacent pairs of struts are joined to form a plurality of proximal and distal apices, the tubular body having a first structural configuration in which the proximal diameter is smaller than the distal diameter and a second structural configuration in which the proximal diameter is larger than the distal diameter; and
at least one helical anchor connected to the tubular body proximate the distal diameter of the frame;
wherein:
angled segments of the frame of the tubular body of the implant form the distal apices of the frame proximate the distal diameter;
a series of holes is provided in at least one of the distal apices of the frame sized and spaced to receive therethrough the at least one helical anchor for rotational engagement of the at least one distal apex by the at least one helical anchor;
the holes of the series of holes in the at least one of the distal apices are oriented to accommodate a pitch of the at least one helical anchor received therethrough; and
the at least one helical anchor is configured to be rotated by a plurality of rotatable drivers through the series of holes to advance the at least one helical anchor distally relative to the frame to penetrate the heart valve annulus.

* * * * *